(12) United States Patent
Johnson et al.

(10) Patent No.: US 10,953,097 B2
(45) Date of Patent: Mar. 23, 2021

(54) ELECTROSPUN FIBERS HAVING CONTRAST AGENTS AND METHODS OF MAKING THE SAME

(71) Applicant: NANOFIBER SOLUTIONS, LLC, Hilliard, OH (US)

(72) Inventors: Jed Johnson, London, OH (US); Devan Ohst, Columbus, OH (US); Jason Chakroff, Columbus, OH (US)

(73) Assignee: NANOFIBER SOLUTIONS. LLC, Hilliard, OH (US)

( * ) Notice: Subject to any disclaimer, the term of this patent is extended or adjusted under 35 U.S.C. 154(b) by 423 days.

(21) Appl. No.: 15/341,924

(22) Filed: Nov. 2, 2016

(65) Prior Publication Data

US 2017/0119886 A1 May 4, 2017

Related U.S. Application Data

(60) Provisional application No. 62/249,640, filed on Nov. 2, 2015.

(51) Int. Cl.
| | |
|---|---|
| *A61K 9/70* | (2006.01) |
| *A61K 47/34* | (2017.01) |
| *A61L 27/54* | (2006.01) |
| *A61L 27/58* | (2006.01) |
| *A61L 27/18* | (2006.01) |
| *A61L 27/50* | (2006.01) |
| *A61K 49/04* | (2006.01) |
| *D01D 5/00* | (2006.01) |
| *A61K 49/00* | (2006.01) |
| *D01F 1/09* | (2006.01) |
| *D01F 1/10* | (2006.01) |

(52) U.S. Cl.
CPC .......... *A61K 47/34* (2013.01); *A61K 49/0002* (2013.01); *A61K 49/0409* (2013.01); *A61L 27/18* (2013.01); *A61L 27/50* (2013.01); *A61L 27/54* (2013.01); *A61L 27/58* (2013.01); *D01D 5/0038* (2013.01); *D01F 1/09* (2013.01); *D01F 1/10* (2013.01)

(58) Field of Classification Search
CPC ......... A61L 17/005; A61K 47/34; A61K 9/70; A61K 9/7007; A61K 47/00; A61K 47/02; A61K 47/06; A61K 47/08; A61K 47/26; A61K 47/36; A61K 47/38; A61K 49/00; A61K 49/0002; A61B 17/12186
See application file for complete search history.

(56) References Cited

U.S. PATENT DOCUMENTS

| | | |
|---|---|---|
| 4,693,721 A | 9/1987 | Ducheyne |
| 4,738,740 A | 4/1988 | Pinchuk et al. |
| 5,258,027 A | 11/1993 | Berghaus |
| 5,628,788 A | 5/1997 | Pinchuk |
| 6,143,022 A | 11/2000 | Shull et al. |
| 6,635,082 B1 | 10/2003 | Hossainy et al. |
| 7,115,220 B2 | 10/2006 | Dubson et al. |
| 7,172,765 B2 | 2/2007 | Chu et al. |
| 7,220,281 B2 | 5/2007 | Lambrecht et al. |
| 7,390,760 B1 | 6/2008 | Chen et al. |
| 7,413,575 B2 | 8/2008 | Phaneuf et al. |
| 7,490,563 B2 | 2/2009 | Eastin et al. |
| 7,629,030 B2 | 12/2009 | Robertson et al. |
| 7,718,351 B2 | 5/2010 | Ying et al. |
| 7,993,567 B2 | 8/2011 | Scott-Carrell et al. |
| 8,157,722 B2 | 4/2012 | Arnal et al. |
| 8,623,085 B2 | 1/2014 | Gatt et al. |
| 8,691,543 B2 | 4/2014 | Gaudette et al. |
| 8,771,582 B2 | 7/2014 | Phaneuf et al. |
| 8,821,441 B2 | 9/2014 | Wilson et al. |
| 10,562,225 B2 | 2/2020 | Johnson |
| 2002/0082707 A1 | 6/2002 | Homsy |
| 2002/0090725 A1* | 7/2002 | Simpson ................. A61L 15/32 435/402 |
| 2002/0142458 A1 | 10/2002 | Williams et al. |
| 2003/0168756 A1 | 9/2003 | Balkus, Jr. et al. |
| 2003/0226750 A1 | 12/2003 | Fenn |
| 2005/0177249 A1 | 8/2005 | Kladakis et al. |
| 2005/0277985 A1 | 12/2005 | Wert et al. |
| 2006/0060999 A1 | 3/2006 | Amagasa et al. |
| 2006/0085063 A1 | 4/2006 | Shastri et al. |

(Continued)

FOREIGN PATENT DOCUMENTS

| | | |
|---|---|---|
| CN | 102008755 A | 4/2011 |
| DE | 102008060708 A1 | 6/2010 |

(Continued)

OTHER PUBLICATIONS

Aboitiz et al. "Fiber composition of the human corpus callosum" (Dec. 11, 1992) *Brain Res.* 598(1-2):143-153 (Abstract only).

Albertini et al. "The effect of glycosaminoglycans and proteoglycans on lipid peroxidation" (Aug. 2000) *Int. J Mol. Med.* 6(2):129-136 (Abstract only).

Alexis et al. "In Vivo Particle Uptake by Airway Macrophages in Healthy Volunteers" (2006) *Am. J. Respir. Cell Mol. Biol.* 34(3):305-313.

Band et al. "Antiproliferative effect of gossypol and its optical isomers on human reproductive cancer cell lines" (Mar. 1989) *Gynecologic Oncology* 32(3):273-277 (Abstract only).

(Continued)

*Primary Examiner* — Micah Paul Young
(74) *Attorney, Agent, or Firm* — Troutman Pepper Hamilton Sanders LLP

(57) ABSTRACT

A fiber may comprise an electrospun polymer and a contrast agent. A method of making an electrospun fiber may comprise configuring a receiving surface to receive a polymer fiber, applying a charge to one or more of the receiving surface, a polymer injection system, and a polymer solution ejected from the polymer injection system, and depositing a polymer solution ejected from the polymer injection system onto the receiving surface. The polymer solution may comprise a polymer and a contrast agent.

23 Claims, 12 Drawing Sheets

(56) References Cited

U.S. PATENT DOCUMENTS

| | | |
|---|---|---|
| 2006/0134157 A1 | 6/2006 | Lehman et al. |
| 2006/0135020 A1 | 6/2006 | Weinburg et al. |
| 2006/0154063 A1 | 7/2006 | Fujihara et al. |
| 2006/0200232 A1 | 9/2006 | Phaneuf et al. |
| 2006/0204539 A1* | 9/2006 | Atala ............... D01D 5/0007 424/423 |
| 2007/0142907 A1 | 6/2007 | Moaddeb et al. |
| 2007/0191956 A1 | 8/2007 | Prewett et al. |
| 2007/0232169 A1 | 10/2007 | Strickler et al. |
| 2007/0269481 A1 | 11/2007 | Li et al. |
| 2007/0286880 A1 | 12/2007 | Vasiliev et al. |
| 2008/0208323 A1 | 8/2008 | El Kurdi et al. |
| 2008/0208358 A1 | 8/2008 | Bellamkonda et al. |
| 2009/0018643 A1 | 1/2009 | Hashi et al. |
| 2009/0108503 A1 | 4/2009 | Scott-Carnell et al. |
| 2009/0143855 A1 | 6/2009 | Weber et al. |
| 2009/0152773 A1 | 6/2009 | Barinov et al. |
| 2009/0162468 A1 | 6/2009 | Barinov et al. |
| 2010/0041292 A1* | 2/2010 | Kim ................... B82Y 30/00 442/181 |
| 2010/0082114 A1 | 4/2010 | Gingras et al. |
| 2010/0105799 A1 | 4/2010 | Rudd et al. |
| 2010/0166854 A1 | 7/2010 | Michniak-Kohn et al. |
| 2010/0222771 A1 | 9/2010 | Mitchell et al. |
| 2010/0233115 A1 | 9/2010 | Patel et al. |
| 2010/0273258 A1 | 10/2010 | Lannutti et al. |
| 2010/0303881 A1 | 12/2010 | Hoke et al. |
| 2011/0022149 A1 | 1/2011 | Cox et al. |
| 2011/0028834 A1 | 2/2011 | Zussman |
| 2011/0030885 A1 | 2/2011 | Anneaux et al. |
| 2011/0070283 A1 | 3/2011 | Hossainy et al. |
| 2011/0083987 A1 | 4/2011 | Rolland et al. |
| 2011/0098826 A1 | 4/2011 | Mauck et al. |
| 2011/0111201 A1* | 5/2011 | Reneker ............... D01D 5/00 428/222 |
| 2011/0166647 A1 | 7/2011 | Hashi et al. |
| 2011/0177395 A1 | 7/2011 | Kamisasa |
| 2011/0270412 A1 | 11/2011 | Bellan et al. |
| 2012/0068384 A1 | 3/2012 | Phaneuf et al. |
| 2012/0093717 A1 | 4/2012 | Mauck et al. |
| 2012/0271405 A1 | 10/2012 | Soletti et al. |
| 2013/0011484 A1 | 1/2013 | Bevier |
| 2013/0066438 A1 | 3/2013 | Seifalian |
| 2013/0103079 A1 | 4/2013 | Lau et al. |
| 2013/0150963 A1 | 6/2013 | Johnson |
| 2013/0183352 A1 | 7/2013 | Xie |
| 2013/0310920 A1 | 11/2013 | Su |
| 2014/0030315 A1 | 1/2014 | Johnson |
| 2014/0057346 A1 | 2/2014 | Johnson |
| 2014/0072951 A1 | 3/2014 | Johnson |
| 2014/0079758 A1 | 3/2014 | Hall et al. |
| 2014/0271795 A1 | 9/2014 | Phaneuf et al. |
| 2014/0272225 A1 | 9/2014 | Johnson |
| 2014/0277572 A1 | 9/2014 | Martin et al. |
| 2014/0309726 A1 | 10/2014 | Wang |
| 2014/0332733 A1* | 11/2014 | Joo ................... D04H 1/4234 252/513 |
| 2015/0132423 A1* | 5/2015 | Johnson ............... A61F 2/20 425/6 |
| 2015/0173772 A1 | 6/2015 | Bowman et al. |
| 2017/0182206 A1 | 6/2017 | Johnson et al. |
| 2017/0319742 A1 | 11/2017 | Johnson et al. |
| 2020/0054976 A1 | 2/2020 | Johnson et al. |

FOREIGN PATENT DOCUMENTS

| | | |
|---|---|---|
| EP | 0416846 A2 | 3/1991 |
| EP | 242203 A | 10/2010 |
| EP | 2422003 | 10/2010 |
| EP | 2813212 A1 | 12/2014 |
| JP | H07059787 A | 3/1995 |
| JP | 2006506171 A | 2/2006 |
| JP | 2012-527217 A | 11/2012 |
| JP | 2013541358 A | 11/2013 |
| WO | WO 91/18612 | 12/1991 |
| WO | WO 2000/010622 A1 | 3/2000 |
| WO | WO 2001/015754 A1 | 3/2001 |
| WO | WO 2005/012606 A2 | 2/2005 |
| WO | 2005096989 A1 | 10/2005 |
| WO | WO 2006/138552 A2 | 12/2006 |
| WO | 2007137653 A1 | 12/2007 |
| WO | 2008118913 A2 | 10/2008 |
| WO | WO 2008/137659 A1 | 11/2008 |
| WO | WO 2009/089035 A1 | 7/2009 |
| WO | WO 2010/040129 A3 | 4/2010 |
| WO | WO 2010/048281 A1 | 4/2010 |
| WO | WO 2010/124207 A1 | 10/2010 |
| WO | WO 2013/078051 A1 | 5/2013 |
| WO | WO 2013/106822 A1 | 7/2013 |
| WO | WO 2014/031721 A1 | 2/2014 |
| WO | WO 2014/145864 A1 | 9/2014 |
| WO | 2015020527 A1 | 2/2015 |
| WO | 2015048224 A1 | 4/2015 |
| WO | 2015100238 A1 | 7/2015 |
| WO | WO 2015/153011 A1 | 10/2015 |
| WO | 2017044982 A1 | 3/2017 |
| WO | WO-2017044982 A1 * | 3/2017 ......... A61B 17/1214 |

OTHER PUBLICATIONS

Bandtlow et al. "Proteoglycans in the developing brain: new conceptual insights for old proteins" (Oct. 2000) *Physiol. Rev.* 80(4):1267-1290.

Baran et al. "Important roles for macrophage colony-stimulating factor, CC chemokine ligand 2, and mononuclear phagocytes in the pathogenesis of pulmonary fibrosis" (2007) *Am. J Respir. Crit. Care Med.* 176(1):78-89.

Bellail et al. "Microregional extracellular matrix heterogeneity in brain modulates glioma cell invasion" (Jun. 2004) *Int. J. Biochem. Cell Biol.* 36(6):1046-1069 (Abstract only).

Beningo et al. "Nascent Focal Adhesions Are Responsible for the Generation of Strong Propulsive Forces in Migrating Fibroblasts" (May 14, 2001) *J. Cell Biol.* 153(4):881-887.

Benz et al. "Biochemical Correlates of the Antitumor and Antimitochondrial Properties of Gossypol Enantiomers" (Jun. 1990) *Mol. Pharma.* 37(6):840-847 (Abstract only).

Benz et al. "Lactic Dehydrogenase Isozymes, $^{31}$P Magnetic-Resonance Spectroscopy, and In Vitro Antimitochondrial Tumor Toxicity With Gossypol and Rhodamine-123" (Feb. 1987) *J. Clin. Invest.* 79(2):517-523.

Benz et al. "Selective toxicity of gossypol against epithelial tumors and its detection by magnetic resonance spectroscopy" (Mar. 1988) *Contraception* 37(3):221-228 (Abstract only).

Bernstein et al. "Glioblastoma cells do not intravasate into blood vessels" (Jan. 1995) *Neurosurgery* 36(1):124-132 (Abstract only).

Bershadsky et al. "Adhesion-mediated mechanosensitivity: a time to experiment, and a time to theorize" (Oct. 2006) *Curr. Opn. Cell Biol.* 18(5):472-481 (Abstract only).

Binder et al. "Proteases and the Biology of Glioma Invasion" (2002) *J. Neuro-Oncology* 56:149-158.

Brown et al., "Synthesis, X-ray Opacity, and Biological Compatibility of Ultra-High Payload Elemental Bismuth Nanoparticle X-ray Contrast Agents" *Chemistry of Materials* (Mar. 10, 2014), (26) pp. 2266-2274.

Bucala et al. "Circulating Fibrocytes Define a New Leukocyte Subpopulation That Mediates Tissue Repair" (Nov. 1994) *Mol. Med.* 1(1):71-81 (Abstract only).

Bull et al., "Self-Assembled Peptide Amphiphile Nanofibers Conjugated to MRI Contrast Agents ", *American Chemical Society* (Jan. 2005), 5(1) pp. 1-4.

Camoretti-Mercado "Targeting the airway smooth muscle for asthma treatment" (Oct. 2009) *Translational Research* 154(4):165-174 (Abstract only).

Cattaruzza et al. "Proteoglycan control of cell movement during wound healing and cancer spreading" (Sep. 2005) *Matrix Biol.* 24(6):400-417 (Abstract only).

(56) References Cited

OTHER PUBLICATIONS

Central Brain Tumor Registry of the United States, Primary Brain Tumors in the United States—Statistical Report 1998-2002, *CBTRUS* 2005-2006.
Chalmers et al. "Chapter 9. Preparative applications of magnetic separation in biology and medicine" (2007) *Laboratory Techniques in Biochemistry and Molecular Biology* 32:249-264 (Abstract only).
Chen et al., Preparation and Characterization of Coaxial Electrospun Thermoplastic Polyurethane/Collagen Compound Nanofibers for Tissue Engineering Applications, *Colloids and Surfaces B-Biointerfaces* (2010), 79(2):315-325.
Chew et al. "The Role of Electrospinning in the Emerging Field of Nanomed eine" 2006, *Curr. Pharm. Sec.* 12(36)A:4751-4770.
Chicoine et al. "Assessment of brain-tumor cell motility in vivo and in vitro" (Apr. 1995) *J. Neurosurg.* 82(4):615-622 (Abstract only).
Choi et al. "Structuring electrospun polycaprolactone nanofiber tissue scaffolds by femtosecond laser ablation" (Nov. 2007) *J. Laser Appl.* 19(4):225-231.
Cukierman et al. "Taking cell-matrix adhesions to the third dimension" (Nov. 23, 2001) *Science* 294:1708-1712.
Davies et al. "Adult axon regeneration in adult CNS white matter" (Dec. 1, 1998) *Trends Neurosci.* 21(12):515.
Delpech et al. "Hyaluronan and hyaluronectin in the nervous system" (Sep. 28, 2007) Ciba Foundation Symposium 143—The Biology of Hyaluronan (Abstract only).
Diaz et al. "Controlled encapsulation of hydrophobic liquids in hydrophilic polymer nanofibers by co-electrospinning" (2006) *Adv. Funct. Mater.* 16(16):2110-2116.
Discher et al. "Tissue cells feel and respond to the stiffness of their substrate" (Nov. 18, 2005) *Science* 310:1139-1143.
Drilling et al. "Fabrication of burst pressure competent vascular grafts via electrospinning: Effects of microstructure" (Mar. 15, 2009) *J. Miomed Mat. Res. Part A* 88A(4):923-934 (Abstract only).
Duling et al. "Mechanical characterization of electrospun Polycaprolactone (PCL): a potential scaffold for tissue engineering" (Feb. 2008) *J. Biomech. Eng.* 130(1) No. 011006 (Abstract only).
Engler et al. "Matrix Elasticity Directs Stem Cell Lineage Specification" (Aug. 25, 2006) *Cell* 126(4):677-689.
Epperly et al. "Correlation of Ionizing Irradiation-induced Late Pulmonary Fibrosis with Longterm Bone Marrow Culture Fibroblast Progenitor Cell Biology in Mice Homozygous Deletion Recombinant Negative for Endothelial Cell Adhesion Molecules" (2004) *In Vivo* 18(1):1-14.
Farin et al. "Transplanted glioma cells migrate and proliferate on host brain vasculature: a dynamic analysis" (Jun. 2006) *Glia* 53(8):799-808 (Abstract only).
Fathallah-Shaykh "Darts in the Dark Cure Animal, but Not Human, Brain Tumors" (May 2002)*Arch. Neural.* 59:721-724 (Abstract only).
Frey et al. "Electrospinning and Porosity Measurements of Nylon6 Peo blended Nonwovens" *Journal of Engineered Fibers and Fabrics* (2007) 2(1):31-37.
Fujihara et al "Guided bone regeneration membrane made of Polycaprolactone/calcium carbonate composite nano-fibers" (Jul. 2005) *Biomaterials* 26(19):4139-4147 (Abstract only).
Furnari et al. "Malignant astrocytic glioma: genetics, biology, and paths to treatment" (2007) *Genes Dev.* 21:2683-2710.
Gaumer et al. "Structure-function relationships and Source-to-ground Distance and the Mechanical Properties of Electrospun Fiber" *Acta Biomaterialia* 5(5):1552-1561 (Abstract only).
Geiser et al. "The Role of Macrophages in the Clearance of Inhaled Ultrafine Titanium Dioxide Particles" (2008) *Am. J. Respir. Cell Mol. Biol.* 38(3):371-376.
Georges et al. "Cell type-specific response to growth on soft materials" (Apr. 2005) *J. Appl. Physiol.* 98:1547-1553.
Georges et al. "Matrices with compliance comparable to that of brain tissue select neuronal over glial growth in mixed cortical cultures" (Apr. 2006) *Biophys. J.* 90:3012-3018.
Giese et al. "Dichotomy of astrocytoma migration and proliferation" (1996) *Int. J. Cancer* 67:275-282.
Giese et al. "Glioma cell adhesion and migration on human brain sections" (1998) *Anticancer Res.* 18(4A):2435-2447 (Abstract only).
Giese et al. "Migration of Human Glioma Cells on Myelin" (Apr. 1996) *Neurosurgery* 38(4):755-764 (Abstract only).
Giese et al. "Substrates for astrocytoma invasion" (Aug. 1995) *Neurosurgery* 37(2):294-302 (Abstract only).
Gilbert et al. "Antiproliferative activity of gossypol and gossypolone on human breast cancer cells" (May 26, 1995) *Life Sciences* 57(1):61-67 (Abstract only).
Gladson "The Extracellular Matrix of Gliomas: Modulation of Cell Function" (Oct. 1999) *J. Neuropath. Exper. Neur.* 58(10):1029-1040 (Abstract only).
Goldbrunner et al. "Cell-extracellular matrix interaction in glioma invasion" (1999) *Acta Neurochir (Wien)* 141:295-305.
Grandpre et al. "Nogo: a molecular determinant of axonal growth and regeneration" (Oct. 2001) *Neuroscientist* 7(5):377-386 (Abstract only).
Haley et al. "Study of myelin purity in relation to axonal contamination" (1980) *Cell Mol. Neurobiol.* 1:175-187.
Hashi et al. "Antithrombogenic Modification of Small Diameter Microfibrous Vascular Grafts" *Arterioscler Thromb Vasc Biol.* (Aug. 2010) 30(8):1621-1627.
Hashi et al. "Antithrombogenic Property of Bone Marrow Mesenchymal Stem Cells in Nanofibrous Vascular Grafts" Jul. 17, 2007, *PNAS* 104(29) pp. 11915-11920.
He et al. "Fabrication of Drug-Loaded Electrospun Aligned Fibrous Threads for Suture Applications" 2009, J. Biomed. Mater. Research, Part A 89(1):80-95.
Hinz et al. "Alpha-smooth muscle actin expression upregulates fibroblast contractile activity" (Sep. 2001) *Molecular Biology of the Cell* 12(9):2730-2741.
Holland "Glioblastoma multiforme; the terminator" (Jun. 6, 2000) *PNAS USA* 97(12):6242-6244.
Hsu et al. "N,N-Dimethylformamide Additions to the Solution for the Electrospinning of Poly(ε-caprolactone) Nanofibers" (Apr. 2004) *Macromolecular Materials and Engineering* 289(4):334-340.
Hsu et al. "Nano-sized beads and porous fiber constructs of Poly(ε-caprolactone) produced by electrospimiing" (2004) *Journal of Material Science* 39(9):3003-3013.
Hu et al. "Gossypol inhibits basal and estrogen-stimulated DNA synthesis in human breast carcinoma cells" (1993) *Life Sciences* 53(25):PL433-PL438 (Abstract only).
Hu et al. "Regulating axon growth within the postnatal central nervous system" (Dec. 2004) *Semin Perinatol* 28(6):371-378.
Hu et al. "The proteoglycan brevican binds to fibronectin after proteolytic cleavage and promotes glioma cell motility" (Sep. 5, 2008) *Journal of Biological Chemistry* 283(36):24848-24859.
Huang et al. "A review on polymer nanofibers by electrospinning and their applications in nanocomposites" (Nov. 2003) *Composites Science and Technology* 63(15):2223-2253 (Abstract only).
International Search Report and Written Opinion for PCT/US2015/016973 dated May 22, 2015.
International Search Report and Written Opinion for PCT/US2016/030058 dated Jul. 29, 2016.
Jaroszewski et al. "Action of Gossypol and Rhodamine 123 on Wild Type and Multidrug-resistant MCF-7 Human Breast Cancer Cells: $^{31}P$ Nuclear Magnetic Resonance and Toxicity Studies" (1990) *Cancer Research* 50(21):6936-6943.
Johnson "First-in-the-World Equine Joint Injection for Osteoarthritis" (Jul./Aug. 2014) *The International Equine Veterinarian* 23-25.
Johnson et al. "Electrospun PCL in Vitro: a Microstructural Basis for Mechanical Property Changes" (2009) *Journal of Biomaterials Science, Polymer Edition* 20(4):467-481 (Abstract only).
Johnson et al. "Microstructure-Property Relationships in a Tissue-Engineering Scaffold" (2007) *Journal of Applied Polymer Science* 104(5):2919-2927.
Johnson et al. "Quantitative Analysis of Complex Glioma Cell Migration on Electrospun Polycaprolcatone Using Time-Lapse Microscopy" (2009) *Tissue Engineering Part C* 15(4):531-540.
Jung et al. "Tracking the invasiveness of human astrocytoma cells by using green fluorescent protein in an organotypical brain slice model" (Jan. 2001) *J. Neurosurgery* 94(1):80-89 (Abstract only).

(56) References Cited

OTHER PUBLICATIONS

Kang et al. Plasma Treatment of Textiles—synthetic Polymer-Base Textiles (2004) AATCC Review 4(11):29-33.

Katta et al. "Continuous electrospinning of aligned polymer nanofibers onto a wire drum collector" (Sep. 28, 2004) Nano Letters 4(11):2215-2218 (Abstract only).

Kazemnejad et al. "Biochemical and Molecular Characterization of Hepatocyte-Like Cells Derived from Human Bone Marrow Mesenchymal Stem Cells on a Novel Three-Dimensional Biocompatible Nanofibrous Scaffold" Feb. 1, 2009, J. Gastronenter. Hepatol. 24(2):278-287.

Khil et al. "Novel fabricated matrix via electrospinning for tissue engineering" (2005) Journal of Biomedical Materials Research Part B—Applied Biomaterials 72B(1):117-124.

Kim et al. "Controlled protein release from electrospun biodegradable fiber mesh composed of poly($\varepsilon$-caprolactone) and poly(ethylene oxide)" (Jun. 29, 2007) International Journal of Pharmaceutics 338 (1-2):276-283 (Abstract only).

Kim et al. "Epithelial cell $\alpha 3\beta 1$ integrin links $\beta$-catenin and Smad signaling to promote myofibroblast formation and pulmonary fibrosis" (Jan. 2009) Journal of Clinical Investigation 119(1):213-224.

Kleihues et al. "The WHO Classification of Tumors of the Nervous System" (Mar. 2002) J. Neuropathol. Exp. Neurol. 61(3):215-225 (Abstract only).

Klim et al. "A Defined Glycosaminoglycan-Binding Substratum for Human Pluripotent Stem Cells" (2010) Nature Methods 7(23):989-996 (Abstract only).

Ko et al. "High Percentage of False-Positive Results of Cytokeratin 19 RT-PCR in Blood: A Model for the Analysis of Illegitimate Gene Expression" (2000) Oncology 59:81-88 (Abstract only).

Kwon et al. "Electrospun nano- to microfiber fabrics made of biodegradable copolyesters: structural characteristics, mechanical properties and cell adhesion potential" (Jun. 2005) Biomaterials 26(18):3929-3939.

Lannutti et al. "Electrospinning for tissue engineering scaffolds" (Apr. 2007) Materials Science and Engineering: C 27(3):504-509.

Leblanc et al. "An in vitro study of inhibitory activity of gossypol, a cottonseed extract, in human carcinoma cell lines" (Dec. 2002) Pharmacological Research 46(6):551-555.

Lee et al. "Characterization of nano-structured poly($\varepsilon$-caprolactone) nonwoven mats via electrospinning" (Feb. 2003) Polymer 44(4):1287-1294.

Lesma et al. "Glycosaminoglycans in nerve injury: I. Low doses glycosaminoglycans promote neurite formation" (Dec. 1, 1996) J. Neurosci. Res. 46(5):565-571.

Levicar et al. "Proteases in brain tumour progression" (2003) Acta Neurochir. (Wien.) 145:825-838.

Levina et al. "Chemotherapeutic drugs and human tumor cells cytokine network" (2008) International Journal of Cancer 123 (9):2031-2040.

Li et al. "A three-dimensional nanofibrous scaffold for cartilage tissue engineering using human mesenchymal stem cells" (Feb. 2005) Biomaterials 26(6):599-609.

Li et al. "Biological response of chondrocytes cultured in three-dimensional nanofibrous poly($\varepsilon$-caprolactone) scaffolds" (Dec. 15, 2003) Journal of Biomedical Materials Research Part A 67A(4):1105-1114.

Li et al. "Electrospinning nanofibers as uniaxially aligned arrays and layer-by-layer stacked films" (Feb. 2004) Advanced Materials 16(4):361-366.

Li et al. "Multilineage differentiation of human mesenchymal stem cells in a three-dimensional nanofibrous scaffold" (Sep. 2005) Biomaterials 26(25):5158-5166.

Liang et al. "Developing gossypol derivatives with enhanced antitumor activity" (1995) Investigational New Drugs 13(3):181-186.

Liu et al. "Function analysis of estrogenically regulated protein tyrosine phosphatase $\gamma$ (PTP$\gamma$) in human breast cancer cell line MCF-7" (2004) Oncogene 23(6):1256-1262.

Liu et al. "Involvement of breast epithelial-stromal interactions in the regulation of protein tyrosine phosphatase -$\gamma$ (PTP$\gamma$) mRNA expression by estrogenically active agents" (2002) Breast Cancer Research and Treatment 71(1):21-35.

Liu et al. The (-)-enantiomer of gossypol possesses higher anticancer potency than racemic gossypol in human breast cancer: (2002) Anticancer Research 22(1A):33-38.

Liu et al. "Transformation of MCF-10A Human Breast Epithelial Cells by Zeranol and Estradiol-17beta" (Nov.-Dec. 2004) Breast J. 10(6):514-521 (Abstract only).

Lo et al. "Cell movement s guided by the rigidity of the substrate" (Jul. 2000) Biophysical Journal 79(1);144-152.

Lotfi et al., "Resilon: A Comprehensive Literature Review", Journal of Dental Research, Dental Clinics, Dental Prospects (2013), 7(3) pp. 119-131.

Luu et al. "Development of a nanostructured DNA delivery scaffold via electrospinning of PLGA and PLGA and PLA-PEG block copolymers" (Apr. 29, 2003) Journal of Controlled Release 89(2):341-353.

Macchiarini et al. "Clinical Transplantation of a Tissue-Engineered Airway" (Dec. 13, 2008) The Lancet 372(9655):2023-2030.

Martins et al. "Electrospun nanostructured scaffolds for tissue engineering applications" (2007) Nanomedical 2(6):929-942.

Mathews, "Preparation and anisotropic mechanical behavior of highly-oriented electrospun poly(butylene terephthalate) fibers" (Aug. 2006) Journal of Applied Polymer Science 101(3):2017-2021.

McClure et al. "A Three-Layered Electrospun Matrix to Mimic Native Arterial Architecture Using Polycaprolactone, Elastin, and Collagen: A Preliminary Study" 2010, Acta Biomaterialia 6:2422-2433.

Meng et al., Electrospun aligned nanofibers composite of MWCNT/polyurethane to enhance vascular endothelium cells proliferation and function, Journal of Nanoscience and Nanotechnology (Jul. 8, 2010) pp. 312-320.

Morawski et al. "Perineuronal nets potentially protect against oxidative stress" (Aug. 2004) Exp. Neurol. 188(2):309-315.

Morgenstern et al. "Chondroitin sulphate proteoglycans in the CNS injury response" (2002) Prog. Brain Res. 137:313-332.

Mori et al. "Fibrocytes contribute to the myofibroblast population in wounded skin and originate from the bone marrow" (Mar. 10, 2005) Experimental Cell Research 304(1):81-90.

Murray et al. "Hyper-responsiveness of IPF/UIP fibroblasts: Interplay between TGF $\beta 1$, IL-13 and CCL2" (2008) 40(10):2174-2182.

Nam et al. "Improved Cellular Infiltration in Electrospun Fiber via Engineered Porosity" (Sep. 2007) Tissue Engineering 13(9):2249-2257.

Nam et al. "Materials selection and residual solvent retention in biodegradable electrospun fibers" (Feb. 5, 2008) Journal of Applied Polymer Science 107(3):1547-1524.

Nam et al. "Modulation of Embryonic Mesenchymal Progenitor Cell Differentiation via Control Over Pure Mechanical Modulus in Electrospun Nanofibers" (Apr. 2011) Acta Biomaterialia 7(4):1516-1524.

Nam et al. "Novel Electrospun Scaffolds for the Molecular Analysis of Chondrocytes Under Dynamic Compression" 2009, Tissue Engineering Part A 15(3):513-523.

Ninomiya et al. "Transforming Growth Factor-$\beta$ Signaling Enhances Transdifferentiation of Macrophages into Smooth Muscle-Like Cells" (2006) Hypertension Research 29(4):269-276.

Norton et al. "Myelination in rat brain: method of myelin isolation" (Oct. 1973) J. Neurochem. 21(4):749-757.

Novak et al. "Extracellular matrix and the brain: components and function" (2000) J. Clin. Neurosci. 7(4):280-290.

Ohnishi et al. "A Novel Model of Glioma Cell Invasion Using Organotypic Brain Slice Culture" (Jul. 15, 1998) Cancer Res. 58:2935-2940.

Palfi et al. "Correlation of in vitro infiltration with glioma histological type in organotypic brain slices" (2004) Br. J. Cancer 91(4):745-752.

Pelham Jr. et al. "Cell locomotion and focal adhesions are regulated by substrate flexibility" (Dec. 1997) PNAS USA 94:13661-13665.

Pham et al., Electrospinning of Polymeric Nanofibers for Tissue Engineering Applications: A Review, Tissue Engineering (2006), 12(5):1197-1211.

(56) References Cited

OTHER PUBLICATIONS

Pilkington "The paradox of neoplastic glial cell invasion of the brain and apparent metastatic failure" (1997) *Anticancer Res.* 17(6B):4103-4105 (Abstract).
Powell et al. "EDC cross-linking improves skin substitute strength and stability" (2006) *Biomaterials* 27(34): 5821-5827.
Properzi et al. "Proteoglycans and Brain Repair" (Feb. 2004) *News Physiol. Sci.* 19:33-38.
Quigley et al. "The relationship between survival and the extent of the resection in patients with supratentorial malignant gliomas" (1991) *Neurosurgery* 29:385-389.
Rao "Molecular mechanisms of glioma invasiveness: the role of proteases" (Jul. 2003) *Nature Reviews Cancer* 3:489-501.
Rath et al. "Compressive Forces Induce Osteogenic Gene Expression in Calvarial Osteoblasts" (2008) *Journal of Biomechanics* 41(5):1095-1103.
Rauch "Extracellular matrix components associated with remodeling processes in brain" (2004) *Cell Mol. Life Sci.* 61:203102045.
Reneker et al. "Nanometre diameter fibres of polymer, produced by electrospinning" (1996) *Nanotechnology* 7(3):216-223.
Rocks et al. "ADAMTS-1 Metalloproteinase Promotes Tumor Development through the Induction of a Stromal Reaction In vivo" (2008) *Cancer Research* 68(22):9541-9550.
Ruoslahti "Brain extracellular matrix" (1996) *Glycobiology* 6(5):489-492.
Sasmono et al. "A macrophage colony-stimulating factor receptor—green fluorescent protein transgene is expressed throughout the mononuclear phagocyte system of the mouse" (2003) *Blood* 101(3):1155-1163.
Saunders et al. "Fibrocyte localization to the airway smooth muscle is a feature of asthma" (Feb. 2009) *Journal of Allergy and Clinical Immunology* 123(2): 376-384.
Schiffer et al. "Cell proliferation and invasion in malignant gliomas" (1997) *Anticancer Research* 17(1A):61-69 (Abstract only).
Schmidt et al. "Identification of Circulating Fibrocytes as Precursors of Bronchial Myofibroblasts in Asthma" (2003) *Journal of Immunology* 171(1):380-389.
Shin et al. "Contractile cardiac grafts using a novel nanofibrous mesh" (Aug. 2004) *Biomaterials* 25(17):3717-3723.
Shin et al. "In Vivo Bone Tissue Engineering Using Mesenchymal Stem Cells on a Novel Electrospun Nanofibrous Scaffold" (Jul. 9, 2004) *Tissue Engineering* 10(1-2):33-41.
Sieben et al. "PCR artifacts in LOH and MSI analysis of microdssected tumor cells" (Nov. 2000) *Human Pathology* 31(11):1414-1419.
Silver et al. "Regeneration beyond the glial scar" (Feb. 2004) *Nature* 5:146-156.
Srikar et al. "Desorption-limited mechanism of release from polymer nanofibers" (2008) *Langmuir* 24(3):965-974.
Stein et al. "Estimating the cell density and invasive radius of three-dimensional glioblastoma tumor spheroids grown in vitro" (Aug. 1, 2007) *Applied Optics* 46(22):5110-5118.
Stitzel et al. "Controlled Fabrication of a Biological Vascular Substitute" 2006, *Biomaterials* 27:1088-1094.
Subramanian et al. "Metastasis to and from the central nervous system—the 'relatively protected site'" (Aug. 2002) *The Lancet Oncology* 3(8):498-507.
Swanson et al. "A quantitative model for differential motility of gliomas in grey and white matter" (Oct. 2000) *Cell Proliferation* 33(5):317-329.
Swanson "Quantifying glioma cell growth and invasion in vitro" (2008) *Mathematical and Computer Modeling* 47:638-648.
Teo et al. "A review on electrospinrting design and nanofibre assemblies" (2006) *Nanotechnology* 17(14):R89-R106.
Teo et al. "Electrospun fibre bundle made of aligned nanofibers over two fixed points" (1978) *Nanotechnology* 16:1878-1884.
Thomas et al. "Effects of gossypol on the cell cycle phases in T-47D human breast cancer cells" (Jul.-Aug. 1991) *Anticancer Research* 11(4):1469-1476 (Abstract only).
Tomlinson et al. "Loss of heterozygosity analysis: Practically and conceptually flawed?" (2002) *Genes Chromosomes & Cancer* 34:349-353.
Tonn et al. "Mechanisms of glioma cell invasion" (2003) *Acta Neurochir* Suppl 88: 163-167.
Toole "Hyaluronan and its binding proteins, the hyaladherins" (1990) *Curr. Opin. Cell Biol.* 2:839-844.
Tse, et al. "Current Status of Pipeline Embolization Device in the Treatment of Intracranial Aneurysms: A review" (Dec. 2013) *World Neurosurgery* 80(6): 829-835.
Tuszynski et al. "Differential cytotoxic effect of gossypol on human melanoma, colon carcinoma, and other tissue culture cell lines" (Feb. 1984) *Cancer Research* 44(2):768-771.
Van Meter et al. "The role of matrix metalloproteinase genes in glioma invasion: co-dependent and interactive proteolysis" (2001) *Journal of Neuro-Oncology* 53:213-235.
Viapiano et al. "Behab/brevican requires ADAMTS-mediated proteolytic cleavage to promote glioma invasion" (2008) *J. Neurooncol.* 88:261-272.
Viapiano et al. "From barriers to bridges: chondroitin sulfate proteoglycans in neuropathology" (Oct. 2006) *Trends Mol. Med.* 12(10):488-496.
Vuorinen et al. "Debulking or biopsy of malignant glioma in elderly people—a 10andomized study" (2003) *Acta Neurochir.* 145:5-10.
Wang et al. "Conjugated Linoleic Acid (CLA) Up-regulates the Estrogen-regulated Cancer Suppressor Gene, Protein Tyrosine Phosphatase γ (PTPγ), in Human Breast Cells" (2006) *Anticancer Research* 26(1A):27-34.
Wang et al. "Effect of gossypol on DNA synthesis and cell cycle progression of mammalian cells in vitro" (Jan. 1984) *Cancer Research* 44(1):35-38.
Wang et al. "Nanofibres and their Influence on Cells for Tissue Regeneration" (2005) *Aust. J. Chem.* 58(10):704-712.
Wang et al. "Increased Circulating Fibrocytes in Asthma with Chronic Airflow Obstruction" (2008) *Am. J. Respir. Crit. Care Med.* 178(6): p. 583-591.
Williams et al. "Anti-glioma effects of protein kinase inhibitors that simultaneously block invasion and proliferation" (Oct. 2007) Abstracts from 12th Annual Meeting of the Society for Neuro-Oncology 9: 486 ET-18 (Abstract only).
Wu et al. "Versican protects cells from oxidative stress-induced apoptosis" (Feb. 2005) *Matrix Biology* 24(1):3-13.
Wu et al. "An in vitro and in vivo study of antitumor effects of gossypol on human SW-13 adrenocortical carcinoma" (1986) *Cancer Research* 49(14):3754-3758.
Wykosky et al. "Soluble monomeric EphrinA1 is released from tumor cells and is a functional ligand for the EphA2 receptor" (2008) *Oncogene* 27(58):7260-7273.
Xie et al. "Encapsulation of protein drugs in biodegradable microparticles by co-axial electrospray" Jan. 15, 2008) *Journal of Colloid and Interface Science* 317(2):469-476.
Xie et al. "White matter inhibitors in CNS axon regeneration failure" (Feb. 2007) *Exp. Neurol.* 209(2):302-312.
Yamaguchi "Lecticans: organizers of the brain extracellular matrix" (2000) *Cell Mol. Life Sci.* 57:276-289.
Yang et al. "Integrin α1β1 and α2β1 are the key regulators of hepatocarcinoma cell invasion across the fibrotic matrix microenvironment" (Dec. 1, 2003) *Cancer Research* 63(23): 8312-8317.
Yoo et al. "Surface-Functionalized Electrospun Nanofibers for Tissue Engineering and Drug Delivery" Jan. 1, 2009, *Advanced Drug Delivery Reviews* 61:1033-1042.
Yoshimoto et al. "A biodegradable nanofiber scaffold by electrospinning and its potential for bone tissue engineering" (May 2003) *Biomaterials* 24(12):2077-2082.
Yu et al. "Production of submicrometer diameter fibers by two-fluid electrospinning" (Sep. 2004) *Adv. Mater.* 16(17):1562-1566.
Zborowski et al. "Red blood cell magnetophoresis" (Apr. 2003) *Biophysical Journal* 84:2638-2645.
Zeng et al. "Enzymatic degradation of poly(L-lactide) and poly(ε-caprolactone) electrospun fibers" (Dec. 15, 2004) *Macromolecular Bioscience* 4(12):1118-1125.

(56) References Cited

OTHER PUBLICATIONS

Zeng et al. "Ultrafine fibers electrospun from biodegradable polymers" (Jul. 25, 2003) *Journal of Applied Polymer Science* 89(4):1085-1092.
Zhang et al. "Electrospinning of gelatin fibers and gelatin/PCL composite fibrous scaffolds" (2005) *J. Biomed. Mater. Res. Part B: Appl. Biomater.* 72B(1):156-165.
Zilla and Human, Prosthetic vascular grafts: Wrong models, wrong questions and no healing. *Biomaterials*, 2007. 28(34): p. 5009-5027.
Zhang et al. "Recent development of polymer nanofibers for biomedical and biotechnological applications" (2005) *Journal of Materials Science—Materials in Medicine* 16(10):933-946.
International Search Report and Written Opinion for International Application No. PCT/US2016/060157 dated Jan. 31, 2017.
Lee et al., "Biomedical Applications of Magnetically Functionalized Organic/Inorganic Hybrid Nanofibers," International Journal of Molecular Sciences (Jun. 15, 2015), 16 pp. 13661-13677.
Samios et al., "In situ compatibilization of polyurethane with poly(ethylene terephthalate)," Department of Chemistry, European Polymer Journal (2000), 36 pp. 937-947.
Ayres et al., "Microvascular Endothelial Cell Migration in Scaffolds of Electrospun Collagen," Wound Repair and Regeneration (Mar. 2005), 13(2):A6 (abstract only).
Park, Lab-made organ implanted for first time (Jul. 14, 2017), CNN.com <http://www.cnn.com/2011/Health/07/07/trachea.transplant/index.html>.
Barnhart et al. "Evaluation of an intra-articular synthetic ligament for treatment of cranial cruciate ligament disease in dogs: a six-month prospective clinical trial" Jun. 2016, Vet Comp Orthop. Traumatol. 29:491-498.
Lieblein et al. "STAT3 can be activated through paracrine signaling in breast epithelial cells" (2008) BMC Cancer 8(302):1-14 :302.
Supplemental European Search Report and Written Opinion for EP15774154 dated Sep. 22, 2017.
Baker et al. "The Potential to Improve Cell Infiltration in Composite Fiber-Aligned Electrospun Scaffolds by the Selective Removal of Sacrificial Fibers", Biomaterials, May 2008, pp. 2348-2358, vol. 29, Issue 15, Elsevier, DOI: 10.1016/j.biomaterials.2008.01.032.
Supplemental European Search Report for EP 16862898 dated May 27, 2019.

\* cited by examiner

Tensile data for 2:8 PET:PU blend.

Tensile data for 2:8 PET:PU blend with 1000wt%Ta added.

ELECTROSPUN FIBERS HAVING CONTRAST AGENTS AND METHODS OF MAKING THE SAME

CROSS-REFERENCE TO RELATED APPLICATIONS

This application claims priority to and benefit of U.S. Provisional Application Ser. No. 62/249,640, filed Nov. 2, 2015, entitled "Electrospun Fibers Having Contrast Agents And Methods Of Making The Same," which is hereby incorporated herein by reference in its entirety.

BACKGROUND

Polymer fibers may be useful for the repair, replacement, or treatment of any organ or tissue within the body, or for the proliferation or differentiation of cells outside the body. Such fibers must be biocompatible so that the body or cells do not reject them, and so that they do not create damaging inflammation. Electrospinning is one method of fabricating such fibers while finely controlling their properties and orientation. In some instances, it may be useful for these fibers to be visualized before, during, and after they are implanted, inserted, or otherwise placed in the body. Fibers with radiopaque properties may be advantageous in these instances. In particular, there exists a need for electrospun polymer fibers with one or more contrast agents dispersed therein, which allows the fibers to be visualized before, during, and after implantation.

SUMMARY

The present disclosure is directed to electrospun fibers having contrast agents, and methods of making such fibers.

In some embodiments, a fiber may comprise an electrospun polymer and a contrast agent. The contrast agent may be dispersed throughout the fiber. In some embodiments, the contrast agent may comprise a powder.

In some embodiments, a method of making an electrospun fiber may comprise configuring a receiving surface to receive a polymer fiber, applying a charge to one or more of the receiving surface, a polymer injection system, and a polymer solution ejected from the polymer injection system, and depositing a polymer solution ejected from the polymer injection system onto the receiving surface. The polymer solution may comprise a polymer and a contrast agent.

DETAILED DESCRIPTION

Figure 1A:
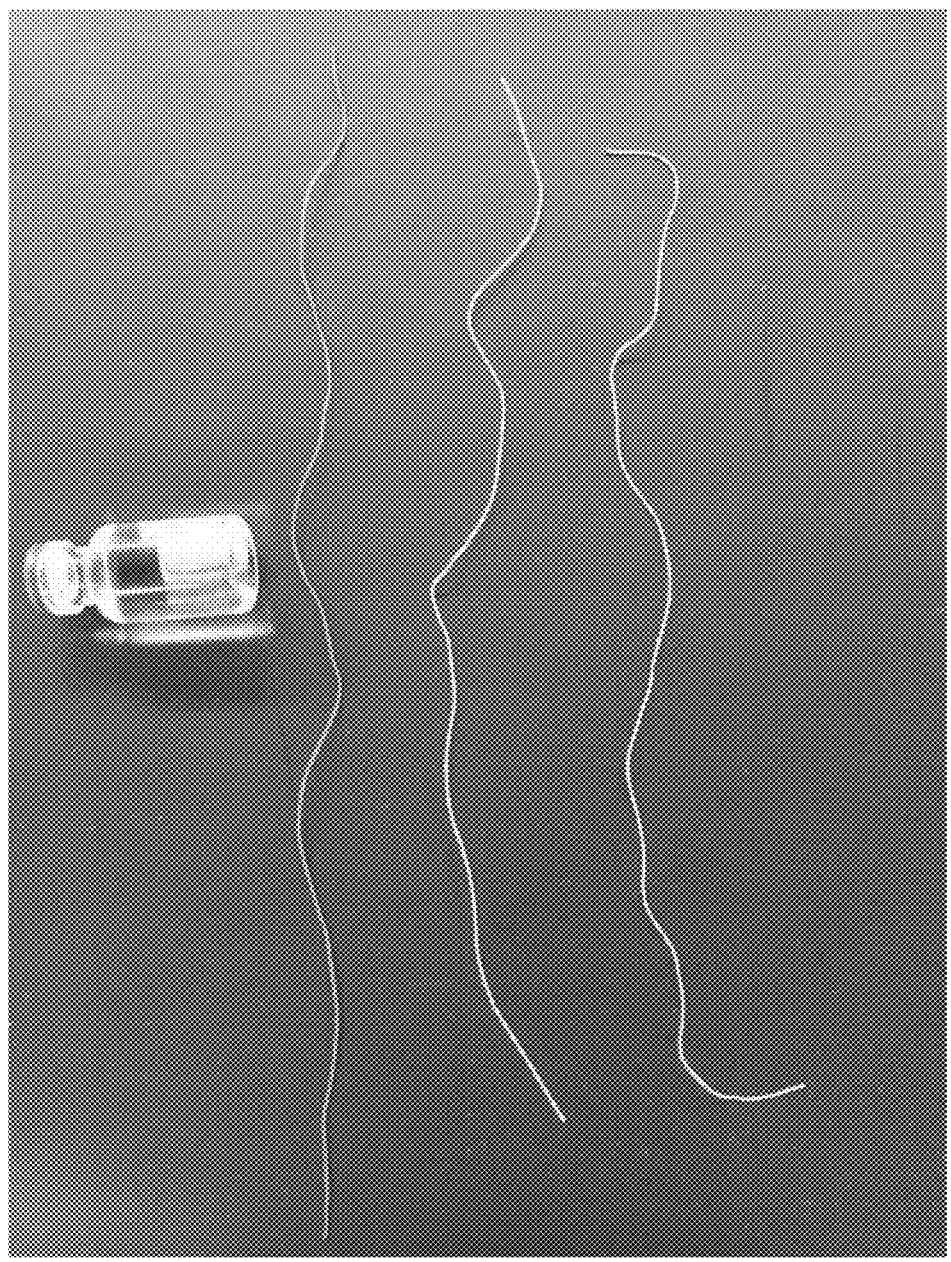
FIG. 1A is a photograph of fibers comprising an electrospun polymer and a contrast agent in accordance with an embodiment of the present disclosure.
Figure 1B:
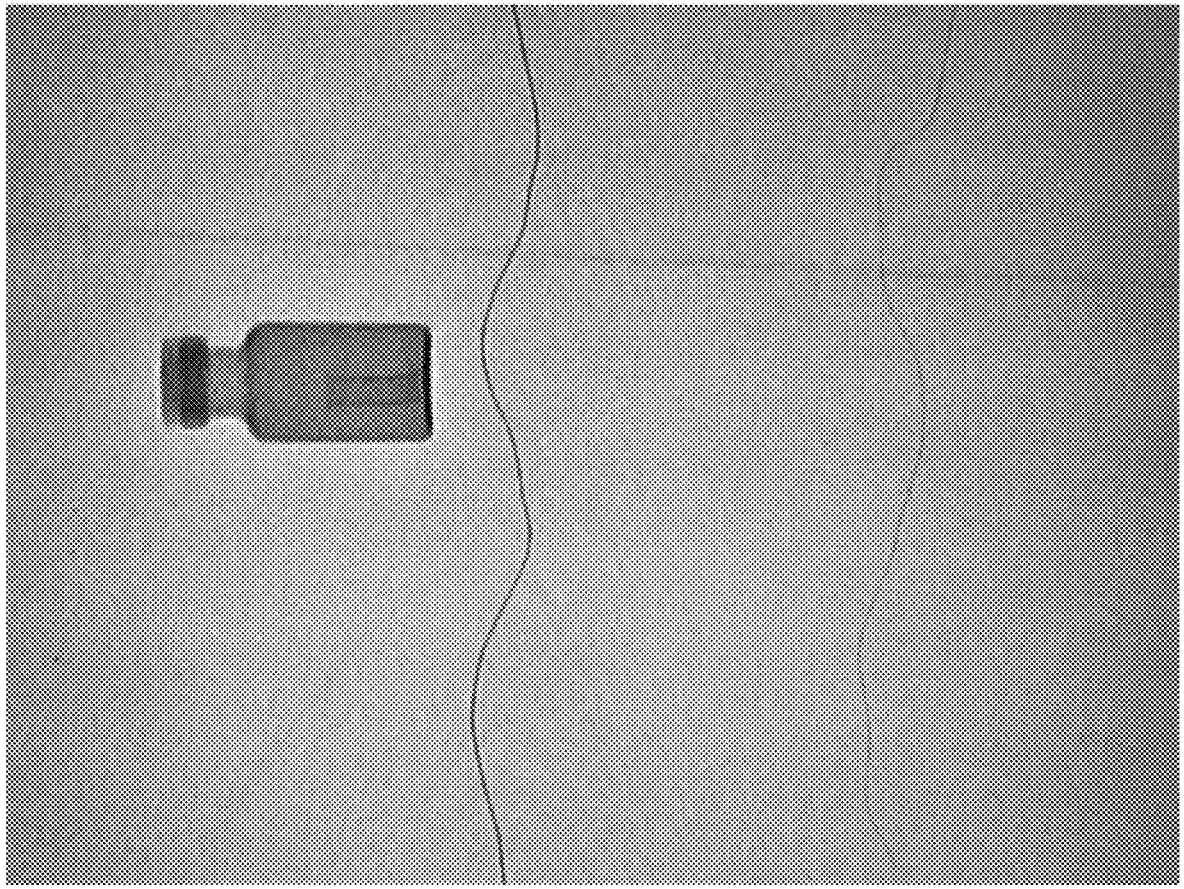
FIG. 1B is an x-ray of the fibers shown in FIG. 1A, showing more contrast on the leftmost thread, no contrast on the middle thread, and less contrast on the rightmost thread compared to a metal stent in the bottle, in accordance with an embodiment of the present disclosure.
Figure 2:
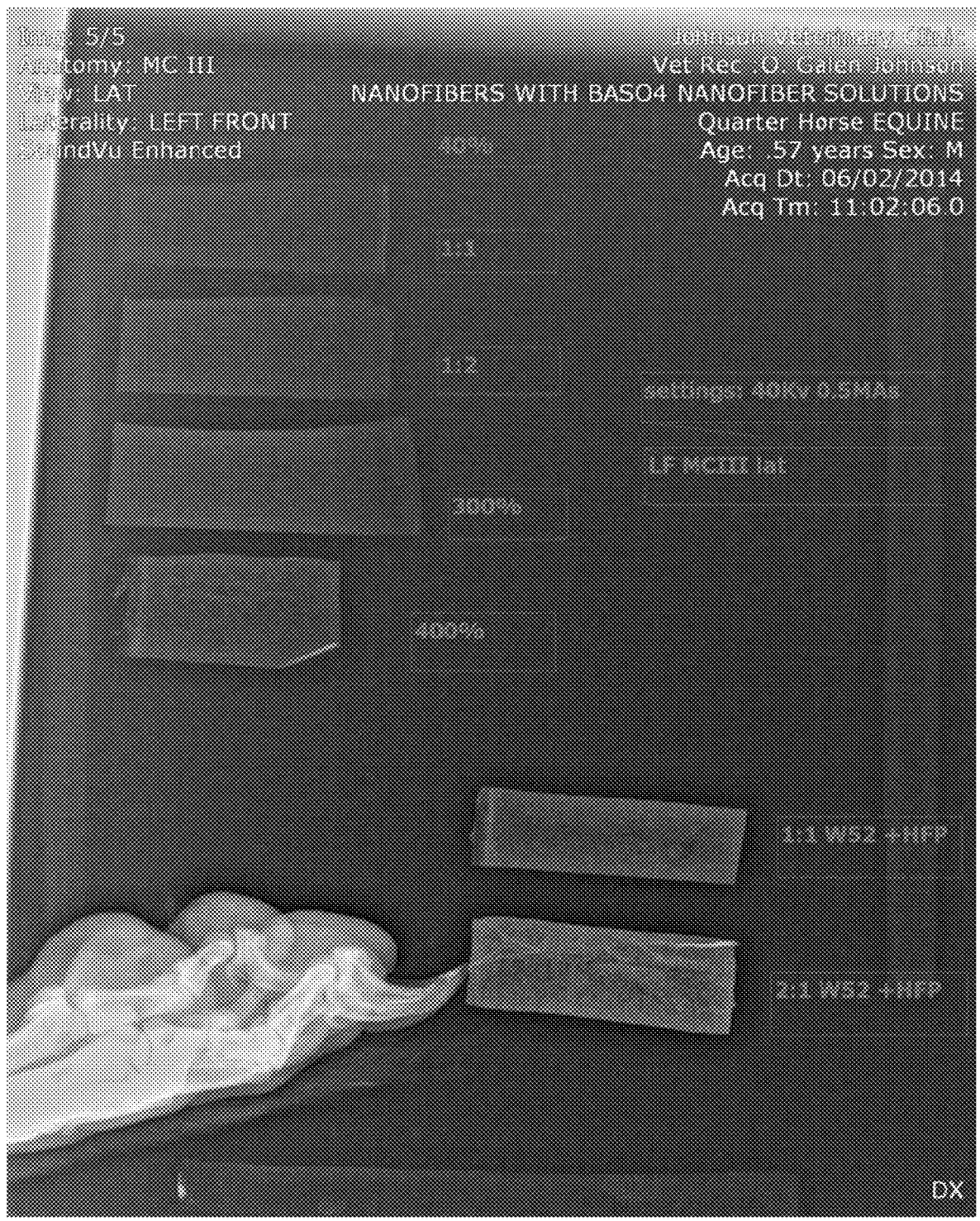
FIG. 2 is an x-ray of fiber sheets comprising barium sulfate and tungsten sulfate in different concentrations, in accordance with an embodiment of the present disclosure. From top to bottom, the x-ray illustrates fiber sheets with concentrations of 40 wt %, 100 wt % (i.e. 1:1), 200 wt % (i.e. 1:2), 300 wt %, 400 wt %, 100 wt %, and 50 wt % (i.e. 2:1) of a combination of barium sulfate and tungsten sulfate based on the weight of the polymer.
Figure 3:
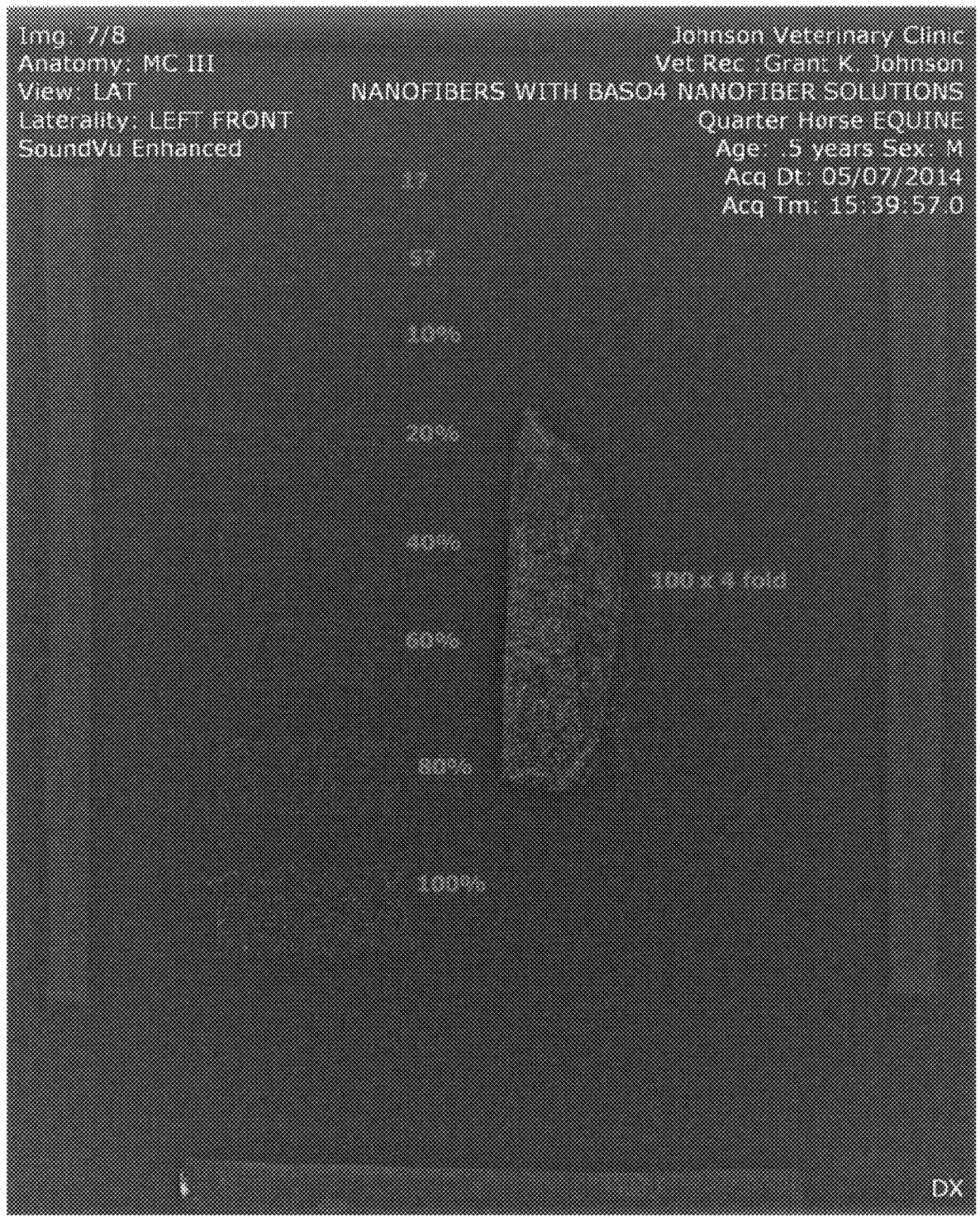
FIG. 3 is an x-ray of fiber sheets comprising different concentrations of barium sulfate, in accordance with an embodiment of the present disclosure. From top to bottom, the x-ray illustrates fiber sheets with concentrations of 1 wt %, 5 wt %, 10 wt %, 20 wt %, 40 wt %, 60 wt %, 80 wt %, and 100 wt % of barium sulfate based on the weight of the polymer.
Figure 4:
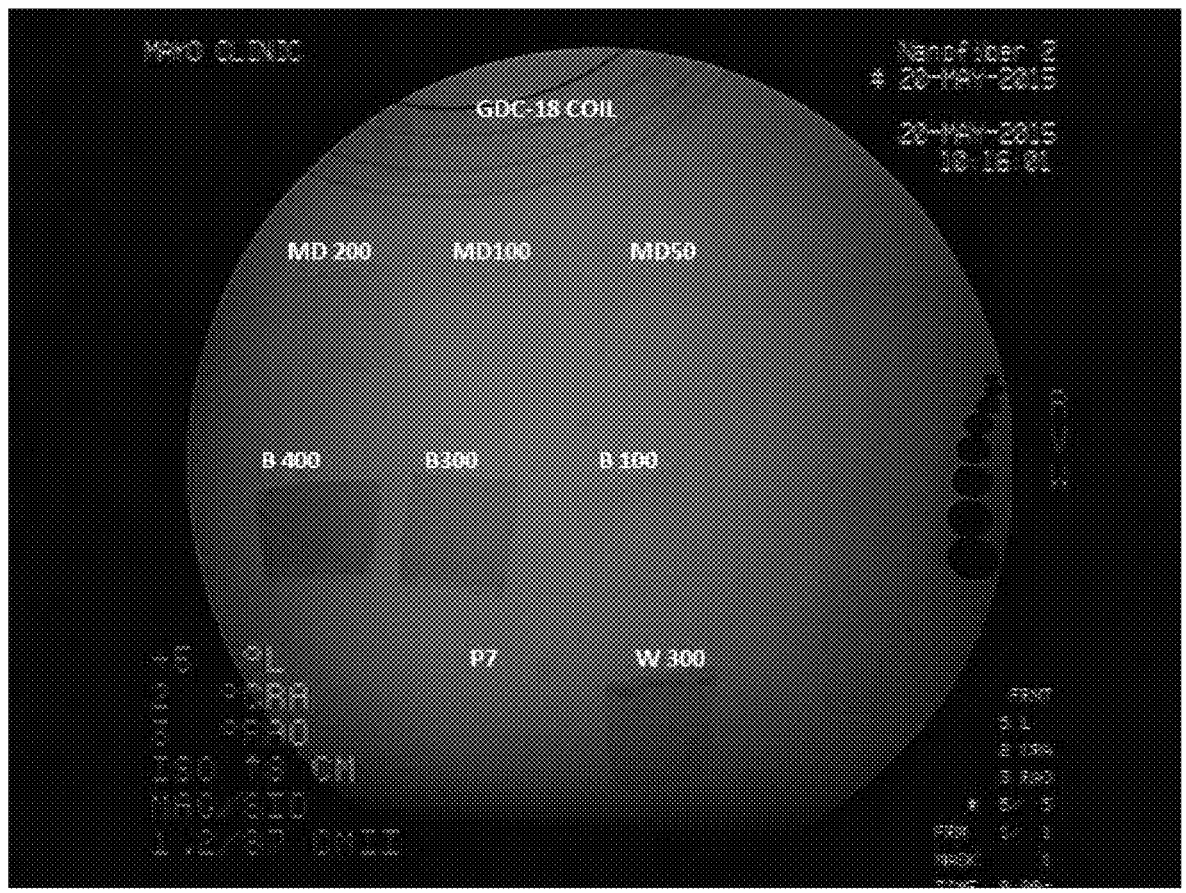
FIG. 4 is an x-ray of fiber sheets comprising barium sulfate and meglumine diatrizoate in different concentrations compared to platinum aneurysm coils, in accordance with an embodiment of the present disclosure.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "fiber" is a reference to one or more fibers and equivalents thereof known to those skilled in the art, and so forth.

As used herein, the term "about" means plus or minus 10% of the numerical value of the number with which it is being used. Therefore, about 50 μm means in the range of 45 μm to 55 μm.

Electrospinning

Electrospinning is a method which may be used to process a polymer solution into a fiber. In embodiments wherein the diameter of the resulting fiber is on the nanometer scale, the fiber may be referred to as a nanofiber. Fibers may be formed into a variety of shapes by using a range of receiving surfaces, such as mandrels, molds, or collectors. The resulting fiber molds or shapes may be used in many applications, including the repair or replacement of biological structures. In some embodiments, the resulting fiber or fiber scaffold may be implanted into a biological organism or a portion thereof.

Electrospinning methods may involve spinning a fiber from a polymer solution by applying a high DC voltage potential between a polymer injection system and a receiving surface. In some embodiments, one or more charges may be applied to one or more components of an electrospinning system. In some embodiments, a charge may be applied to the receiving surface, the polymer injection system, the polymer solution, or combinations or portions thereof. Without wishing to be bound by theory, as the polymer solution is ejected from the polymer injection system, it is thought to be destabilized due to its exposure to a charge. The destabilized solution may then be attracted to a charged receiving surface. As the destabilized solution moves from the polymer injection system to the receiving surface, its solvents may evaporate and the polymer may stretch, leaving a long, thin fiber that is deposited onto the receiving surface. The polymer solution may form a Taylor cone as it is ejected from the polymer injection system and exposed to a charge.

Polymer Injection System

A polymer injection system may include any system configured to eject some amount of a polymer solution into an atmosphere to permit the flow of the polymer solution from the injection system to the receiving surface. In some embodiments, the polymer injection system may deliver a continuous or linear stream with a controlled volumetric flow rate of a polymer solution to be formed into a fiber. In some embodiments, the polymer injection system may deliver a variable stream of a polymer solution to be formed into a fiber. In some embodiments, the polymer injection system may be configured to deliver intermittent streams of a polymer solution to be formed into multiple fibers. In some embodiments, the polymer injection system may include a syringe under manual or automated control. In some embodiments, the polymer injection system may include multiple syringes and multiple needles or needle-like components under individual or combined manual or automated control. In some embodiments, a multi-syringe polymer injection system may include multiple syringes and multiple needles or needle-like components, with each syringe containing the same polymer solution. In some embodiments, a multi-syringe polymer injection system may include multiple syringes and multiple needles or needle-like components, with one or more syringes containing one or more different polymer solutions. In some embodiments, a charge may be applied to the polymer injection system, or to a portion thereof. In some embodiments, a charge may be applied to a needle or needle-like component of the polymer injection system.

In some embodiments, the polymer solution may be ejected from the polymer injection system at a flow rate per needle of less than or equal to about 5 mL/h. Some non-limiting examples of flow rates per needle may include about 0.1 mL/h, about 0.5 mL/h, about 1 mL/h, about 1.5 mL/h, about 2 mL/h, about 2.5 mL/h, about 3 mL/h, about 3.5 mL/h, about 4 mL/h, about 4.5 mL/h, about 5 mL/h, or ranges between any two of these values, including endpoints. As the polymer solution travels from the polymer injection system toward the receiving surface, the diameter of the resulting fibers may be in the range of about 0.1 μm to about 10 μm. Some non-limiting examples of electrospun fiber diameters may include about 0.1 μm, about 0.2 μm, about 0.5 μm, about 1 μm, about 2 μm, about 5 μm, about 10 μm, about 15 μm, about 20 μm, or ranges between any two of these values, including endpoints.

Polymer Solution

In some embodiments, the polymer injection system may be filled with a polymer solution. In some embodiments, the polymer solution may comprise one or more polymers. In some embodiments, the polymer solution may be a fluid formed into a polymer liquid by the application of heat. A polymer solution may include synthetic or semi-synthetic polymers such as, without limitation, polyethylene terephthalate (PET), polyester, polymethylmethacrylate, polyacrylonitrile, silicone, polyurethane, polycarbonate, polyether ketone ketone, polyether ether ketone, polyether imide, polyamide, polystyrene, polyether sulfone, polysulfone, polyvinyl alcohol (PVA), polyvinyl acetate (PVAc), polycaprolactone (PCL), polylactic acid (PLA), polylactide co-caprolactone, polylactide co-glycolide, polyglycolic acid (PGA), polyglycerol sebacic, polydiol citrate, polyhydroxy butyrate, polyether amide, polydioxanone, and combinations or derivatives thereof. In some embodiments, polyhydroxyalkanoates, specifically poly-4-Hydroxybutyrate, may be excluded from the polymer solution described herein. Alternative polymer solutions used for electrospinning may include natural polymers such as fibronectin, collagen, gelatin, hyaluronic acid, chitosan, or combinations thereof. It may be understood that polymer solutions may also include a combination of synthetic polymers and naturally occurring polymers in any combination or compositional ratio. In some non-limiting examples, the polymer solution may comprise a weight percent ratio of, for example, polyethylene terephthalate to polyurethane, from about 10% to about 90%. Non-limiting examples of such weight percent ratios may include 10%, 25%, 33%, 50%, 66%, 75%, 90%, or ranges between any two of these values, including endpoints.

In some embodiments, the polymer may be present in an amount of about 1 wt % to about 30 wt % based on the weight of the polymer solution. In some non-limiting examples, the polymer may be present in the amount of, for example, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, or ranges between any two of these values, including endpoints.

In some embodiments, the polymer solution may comprise one or more solvents. In some embodiments, the solvent may comprise, for example, acetone, dimethylformamide, dimethylsulfoxide, N-methylpyrrolidone, acetonitrile, hexanes, ether, dioxane, ethyl acetate, pyridine, toluene, xylene, tetrahydrofuran, trifluoroacetic acid, hexafluoroisopropanol, acetic acid, dimethylacetamide, chloroform, dichloromethane, water, alcohols, ionic compounds, or combinations thereof. The concentration range of polymer or polymers in solvent or solvents may be, without limitation, from about 1 wt % to about 50 wt %. Some non-limiting examples of polymer concentration in solution may include about 1 wt %, 3 wt %, 5 wt %, about 10 wt %, about 15 wt %, about 20 wt %, about 25 wt %, about 30 wt %, about 35 wt %, about 40 wt %, about 45 wt %, about 50 wt %, or ranges between any two of these values, including endpoints.

In some embodiments, the polymer solution may also include additional materials. Non-limiting examples of such additional materials may include radiation opaque materials, contrast agents, electrically conductive materials, fluorescent materials, luminescent materials, antibiotics, growth factors, vitamins, cytokines, steroids, anti-inflammatory drugs, small molecules, sugars, salts, peptides, proteins, cell factors, DNA, RNA, or any other materials to aid in non-invasive imaging, or any combination thereof. In some embodiments, the electrically conductive materials may include, for example, gold, silver, iron, polyaniline, carbon black, polyacrylonitrile, graphene, or combinations thereof.

In some embodiments, the contrast agents may include, for example, barium, tantalum, tungsten, platinum, gold, bismuth, iodine, gadolinium, diatrizoate, metrizoate, ioxaglate, iopamidol, iohexol, ioxilan, iopromide, iodixanol, derivatives thereof, oxides thereof, salts thereof, or combinations thereof. In some embodiments, the contrast agent may be dispersed in a solution different from the polymer solution described in other embodiments herein. In some embodiments, the contrast agent may be dispersed in the polymer solution. In other embodiments, the contrast agent can be dispersed in a separate solution prior to being added to the polymer solution. In some embodiments, the contrast agent may comprise a powder. In some embodiments, the powder may comprise particles having a diameter from about 10 nm to about 10 μm. In some embodiments, the powder may comprise particles having a diameter of, for example, about 10 nm, about 20 nm, about 30 nm, about 40 nm, about 50 nm, about 60 nm, about 70 nm, about 80 nm, about 90 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 μm, about 2 μm, about 3 μm, about 4 μm, about 5 μm, about 6 μm, about 7 μm, about 8 μm, about 9 μm, about 10 μm, or ranges between any two of these values, including endpoints.

The type of polymer in the polymer solution may determine the characteristics of the electrospun fiber. Some fibers may be composed of polymers that are bio-stable and not absorbable or biodegradable when implanted. Such fibers may remain generally chemically unchanged for the length of time in which they remain implanted. Alternatively, fibers may be composed of polymers that may be absorbed or biodegraded over time. Such fibers may act as an initial template or scaffold for the repair or replacement of organs and/or tissues. These organ or tissue templates or scaffolds may degrade in vivo once the tissues or organs have been replaced or repaired by natural structures and cells. It may be further understood that a polymer solution and its resulting electrospun fiber(s) may be composed of more than one type of polymer, and that each polymer therein may have a specific characteristic, such as bio-stability or biodegradability.

Applying Charges to Electrospinning Components

In an electrospinning system, one or more charges may be applied to one or more components, or portions of components, such as, for example, a receiving surface, a polymer injection system, a polymer solution, or portions thereof. In some embodiments, a positive charge may be applied to the polymer injection system, or portions thereof. In some embodiments, a negative charge may be applied to the polymer injection system, or portions thereof. In some embodiments, the polymer injection system, or portions thereof, may be grounded. In some embodiments, a positive charge may be applied to the polymer solution, or portions thereof. In some embodiments, a negative charge may be applied to the polymer solution, or portions thereof. In some embodiments, the polymer solution, or portions thereof, may be grounded. In some embodiments, a positive charge may be applied to the receiving surface, or portions thereof. In some embodiments, a negative charge may be applied to the receiving surface, or portions thereof. In some embodiments, the receiving surface, or portions thereof, may be grounded. In some embodiments, one or more components or portions thereof may receive the same charge. In some embodiments, one or more components, or portions thereof, may receive one or more different charges.

The charge applied to any component of the electrospinning system, or portions thereof, may be from about −15 kV to about 30 kV, including endpoints. In some non-limiting examples, the charge applied to any component of the electrospinning system, or portions thereof, may be about −15 kV, about −10 kV, about −5 kV, about −3 kV, about −1 kV, about −0.01 kV, about 0.01 kV, about 1 kV, about 5 kV, about 10 kV, about 12 kV, about 15 kV, about 20 kV, about 25 kV, about 30 kV, or any range between any two of these values, including endpoints. In some embodiments, any component of the electrospinning system, or portions thereof, may be grounded.

Receiving Surface Movement During Electrospinning

During electrospinning, in some embodiments, the receiving surface may move with respect to the polymer injection system. In some embodiments, the polymer injection system may move with respect to the receiving surface. The movement of one electrospinning component with respect to another electrospinning component may be, for example, substantially rotational, substantially translational, or any combination thereof. In some embodiments, one or more components of the electrospinning system may move under manual control. In some embodiments, one or more components of the electrospinning system may move under automated control. In some embodiments, the receiving surface may be in contact with or mounted upon a support structure that may be moved using one or more motors or motion control systems. The pattern of the electrospun fiber deposited on the receiving surface may depend upon the one or more motions of the receiving surface with respect to the polymer injection system. In some embodiments, the receiving surface may be configured to rotate about its long axis. In one non-limiting example, a receiving surface having a rotation rate about its long axis that is faster than a translation rate along a linear axis may result in a nearly helical deposition of an electrospun fiber, forming windings about the receiving surface. In another example, a receiving surface having a translation rate along a linear axis that is faster than a rotation rate about a rotational axis may result in a roughly linear deposition of an electrospun fiber along a liner extent of the receiving surface.

Electrospun Fibers Having Contrast Agents

In some embodiments, a fiber may comprise an electrospun polymer and a contrast agent. In some embodiments, a fiber may have a contrast agent dispersed therein. In one embodiment, the fiber includes a contrast agent dispersed within the electropsun polymer. In certain embodiments, the contrast agent is dispersed within the electrospun polymer and excludes contrast agents present only on the outer surface of a fiber formed from the electrospun polymer. Such embodiments exclude dipping, spraying or otherwise treating the outside surface of a fiber with contrast agents. Contrast agents dispersed within the electrospun polymer provide the added benefit of being resistant to accidental or unanticipated removal of the contrast agent from the fiber.

In some embodiments, the electrospun polymer may comprise one or more polymers. In some embodiments, the polymers may include, without limitation, the polymers described above. In some embodiments, polyhydroxyalkanoates, specifically poly-4-Hydroxybutyrate, may be excluded from the polymer solution described herein. It may be understood that polymers may also include a combination of synthetic polymers and naturally occurring polymers in any combination or compositional ratio.

In some embodiments, the contrast agent may comprise, for example, barium, tantalum, tungsten, platinum, gold, bismuth, iodine, gadolinium, diatrizoate, metrizoate, ioxaglate, iopamidol, iohexol, ioxilan, iopromide, iodixanol, derivatives thereof, oxides thereof, salts thereof, or combinations thereof. In some embodiments, the contrast agent may comprise a powder. In some embodiments, the contrast agent may be dispersed in a solution. In some embodiments, the powder may be dispersed in a solution. In some embodiments, the powder may comprise particles having a diameter from about 10 nm to about as described above. In other embodiments, the powder may comprise particles having a diameter from about 10 nm to about 10 µm.

In some embodiments, the contrast agent may be present in an amount of about 10 wt % to about 500 wt %, based on the weight of the polymer. The term "wt %" as used herein refers to the percent weight of the identified material based on the total weight of a formulation containing the identified material. For example, a contrast agent being present in an amount of about 500 wt %, based on the weight of a polymer equates to a final formulation where the concentration of the contrast agent is five times greater than the total weight of the polymer. In one embodiment, the contrast agent may be present in an amount of about 10 wt % to about 2,000 wt %. In some embodiments, the contrast agent may be present in an amount of about 500 wt % to about 2,000 wt %. In another embodiment, the contrast agent may be present in an amount of about 750 wt % to about 1,500 wt %. In one embodiment, the contrast agent is present in an amount of about 900 wt % to about 1,100 wt %. In other embodiments, the contrast agent may be present in an amount of about 850 wt % to about 1,150 wt %. In some embodiments, the contrast agent may be present in an amount of, for example, about 10 wt %, about 20 wt %, about 30 wt %, about 40 wt %, about 50 wt %, about 60 wt %, about 70 wt %, about 80 wt %, about 90 wt %, about 100 wt %, about 125 wt %, about 150 wt %, about 175 wt %, about 200 wt %, about 225 wt %, about 250 wt %, about 275 wt %, about 300 wt %, about 325 wt %, about 350 wt %, about 375 wt %, about 400 wt %, about 425 wt %, about 450 wt %, about 475 wt %, about 500 wt %, about 525 wt %, about 550 wt %, about 575 wt %, about 600 wt %, about 625 wt %, about 650 wt %, about 675 wt %, about 700 wt %, about 725 wt %, about 750 wt %, about 775 wt %, about 800 wt %, about 825 wt %, about 850 wt %, about 875 wt %, about 900 wt %, about 925 wt %, about 950 wt %, about 975 wt %, about 1,000 wt %, about 1,100 wt %, about 1,200 wt %, about 1,300 wt %, about 1,400 wt %, about 1,500 wt %, about 1,600 wt %, about 1,700 wt %, about 1,800 wt %, about 1,900 wt %, about 2,000 wt %, or ranges between any two of these values, including endpoints, based on the weight of the polymer. In some embodiments, the contrast agent may be present in an amount of greater than about 100 wt %, greater than about 150 wt %, greater than about 200 wt %, greater than about 250 wt %, greater than about 300 wt %, greater than about 350 wt %, greater than about 400 wt %, greater than about 450 wt %, greater than about 500 wt %, greater than about 600 wt %, greater than about 700 wt %, greater than about 800 wt %, greater than about 900 wt %, greater than about 1,000 wt %, greater than about 1,500 wt %, greater than about 2,000 wt % or ranges between any two of these values, including endpoints, based on the weight of the polymer. In one embodiment, the contrast agent is present in an amount of about 1,000 wt %.

Electrospinning polymers including contrast agents provides a mechanism to include high concentrations of contrast agent within a fiber formed from the polymers. Other processing methods, such as extrusion techniques, are limited in the amount of solids that can be present within the extruded polymer. Since extruded polymers require some degree of mechanical integrity in order to withstand the extruding process, extruded polymers cannot hold high concentrations of solids. An extruded polymer having a high solids content will exhibit an increase in viscosity and/or will result in a final extruded product having no, or poor, mechanical integrity. In contrast, the electrospun fibers disclosed herein are capable of being formed from electrospun polymers having a high solids content (i.e., particle loading level) while at the same time providing an electrospun fiber having a high degree of mechanical integrity, as demonstrated, for example, in FIGS. 7, 8, and 9. Electrospun polymers, as described herein, may be loaded with a high concentration of particles, including contrast agents. Examples of such high loading concentrations are disclosed herein. The high loading concentrations of the electrospun polymers unexpectedly result in a fiber that maintains sufficient tensile strength, modulus, and elongation as compared to a fiber produced via a typical melt process, i.e., extruding, which suffers extreme loss of strength and elongation. For example, in one embodiment, an electrospun polymer described herein can be loaded with about 1,000 wt % of particles, resulting in a fiber that maintains sufficient tensile strength, modulus, and elongation. Typical melt-processing techniques are limited in the amount of filler that can be present in a polymer before suffering losses in mechanical integrity in an extruded product. For example, increases in filler content of a typical PVC formulation have been shown to decrease the extension at break and tensile strength (See Deshmukh. S. P et al., "Effects of Particle Size and Concentration on Mechanical and Electrical Properties of the Mica Filled PVC," *Journal of Minerals & Materials Characterization & Engineering*, Vol. 9, No. 9, pp. 831-844 (2010)). Further, thermoset systems also illustrate a decrease in tensile strength and elongation (%) with increasing filler content (See Ozsoy, Iskender et al., "The Influence of Miroand Nano-Filler Content on the Mechanical Properties of Epoxy Composites," Journal of Mechanical Engineering, 61.10, pp. 601-609 (2015)). Typical melt process systems have been shown to have the best synthetic properties at about a 25% filler load, after which the synthetic properties vastly erode (See Zhang, S. et al. "The effects of particle size and content on the thermal conductivity and mechanical properties of $Al_2O_3$/high density polyethylene (HDPE) composites," *eXPRESS Polymer Letters*, Vol. 5, No. 7, pp. 581-590 (2011)). Thus, filler loadings of typical melt process polymers of over around 25%-50 wt % have been shown to negatively affect impact strength, elongation and other mechanical properties of typical melt-process polymeric systems. In contrast, it has been observed that fibers according to an embodiment of the instant disclosure, i.e., fibers made from electrospun polymers having high concentrations of filler (including contrast agents), retain mechanical sufficient mechanical integrity that is unexpected in view of the prior art melt-process systems. In addition, an electrospun polymer having a high concentration of contrast agent results in a fiber being highly visible when viewed non-invasively with an imaging method such as X-ray or fluoroscopy, for example. Therefore, in some embodiments, it is desirable to maximize the concentration of the contrast agent in the electrospun polymers. In some embodiments, the contrast agent may be present an amount that maximizes the concentration of the contrast agent in the electrospun polymer while at the same time retaining the integrity of a fiber formed from the polymer solution.

In some embodiments, the contrast agent may allow the fiber to be viewed and monitored with standard radiological imaging techniques, such as, for example, X-ray, fluoroscopy, ultrasound, optical coherence tomography (OCT), computed tomography (CT), magnetic resonance imaging (MRI), or positron emission tomography (PET), before, during, and following its insertion into body or tissue.

In some embodiments, the fiber may further comprise one or more of an electrically conductive material, a fluorescent material, a luminescent material, an antibiotic, a growth factor, a vitamin, a cytokine, a steroid, an anti-inflammatory drug, a small molecule, a sugar, a salt, a peptide, a protein, a cell factor, DNA, RNA, or a combination thereof. In some embodiments, the electrically conductive material may comprise, for example, gold, silver, iron, polyaniline, carbon black, polyacrylonitrile, graphene, or a combination thereof.

In some embodiments, the fiber may have a length from about 5 μm to about 5 m. In some embodiments, the fiber may have a length of, for example, about 5 μm, about 10 μm, about 20 μm, about 30 μm, about 40 μm, about 50 μm, about 60 μm, about 70 μm, about 80 μm, about 90 μm, about 100 μm, about 150 μm, about 200 μm, about 250 μm, about 300 μm, about 400 μm, about 500 μm, about 600 μm, about 700 μm, about 800 μm, about 900 μm, about 1 mm, about 5 mm, about 10 mm, about 20 mm, about 30 mm, about 40 mm, about 50 mm, about 60 mm, about 70 mm, about 80 mm, about 90 mm, about 100 mm, about 150 mm, about 200 mm, about 250 mm, about 300 mm, about 350 mm, about 400 mm, about 450 mm, about 500 mm, about 550 mm, about 600 mm, about 650 mm, about 700 mm, about 750 mm, about 800 mm, about 850 mm, about 900 mm, about 950 mm, about 2 m, about 2 m, about 3 m, about 4 m, about 5 m, or ranges between any two of these values, including endpoints.

In some embodiments, the fiber may have a diameter of about 50 nm to about 50 μm. In some embodiments, the fiber may have a diameter of, for example, about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 μm, about 2 μm, about 3 μm, about 4 μm, about 5 μm, about 10 μm, about 15 μm, about 20 μm, about 25 μm, about 30 μm, about 35 μm, about 40 μm, about 45 μm, about 50 μm, or ranges between any two of these values, including endpoints.

In some embodiments, the fiber may be formed into a shape such as, for example, a fragment, a cluster, a strand, a thread, a rope, a braid, a sheet, a coil, a tube, a cylinder, a textile, or a mold of an organ. In some embodiments, the fiber may be formed into a mold of an organ such as, for example, a trachea, a trachea and at least a portion of at least one bronchus, a trachea and at least a portion of a larynx, a larynx, an esophagus, a large intestine, a small intestine, an upper bowel, a lower bowel, a vascular structure, an artery, a vein, a nerve conduit, a ligament, a tendon, and portions thereof. In some embodiments, the fiber may be formed into the shape of a suture.

In some embodiments, the fiber may be formed into a fragment having an average length of about 1 μm to about 1000 μm, and an average diameter of about 0.1 μm to about 10 μm. Some non-limiting examples of average fragment lengths may include an average length of about 1 μm, about 5 μm, about 10 μm, about 20 μm, about 30 μm, about 40 μm, about 50 μm, about 75 μm, about 90 μm, about 95 μm, about 100 μm, about 105 μm, about 110 μm, about 150 μm, about 200 μm, about 300 μm, about 400 μm, about 500 μm, about 600 μm, about 700 μm, about 800 μm, about 900 μm, about 1000 μm, or ranges between any two of these values (including endpoints). Some non-limiting examples of average fragment diameters may include an average diameter of about 0.1 μm, about 0.5 μm, about about 2 μm, about 3 μm, about 4 μm, about 5 μm, about 6 μm, about 7 μm, about 8 μm, about 9 μm, about 10 μm, or ranges between any two of these values, including endpoints.

In some embodiments, the fiber may be formed into a cluster. As used herein, the term "cluster" refers to an aggregate of fiber fragments, or a linear or curved three-dimensional group of fiber fragments. Clusters may have a range of shapes. Non-limiting examples of cluster shapes may include spherical, globular, ellipsoidal, and flattened cylinder shapes. Clusters may have, independently, an average length of about 1 μm to about 10,000 μm (1 cm), an average width of about 1 μm to about 10,000 μm (1 cm), and an average height of about 1 μm to about 10,000 μm (1 cm). It may be appreciated that any cluster dimension, such as length, width, or height, is independent of any other cluster dimension. Some non-limiting examples of average cluster dimensions include an average dimension (i.e. length, width, height, or other measurement) of about 1 μm, about 5 μm, about 10 μm, about 20 μm, about 30 μm, about 40 μm, about 50 μm, about 75 μm, about 90 μm, about 95 μm, about 100 μm, about 105 μm, about 110 μm, about 150 μm, about 200 μm, about 300 μm, about 400 μm, about 500 μm, about 600 μm, about 700 μm, about 800 μm, about 900 μm, about 1,000 μm, about 1,500 μm, about 2,000 μm, about 2,500 μm, about 3,000 μm, about 3,500 μm, about 4,000 μm, about 4,500 μm, about 5,000 μm, about 5,500 μm, about 6,000 μm, about 6,500 μm, about 7,000 μm, about 7,500 μm, about 8,000 μm, about 8,500 μm, about 9,000 μm, about 9,500 μm, about 10,000 μm (1 cm), or ranges between any two of these values (including endpoints), or independent combinations of any of these ranges of dimensions. Clusters may include an average number of about 2 to about 1000 fiber fragments. Some non-limiting examples of average numbers of fiber fragments per cluster include an average of about 2 fiber fragments per cluster, about 5 fiber fragments per cluster, about 10 fiber fragments per cluster, about 20 fiber fragments per cluster, about 30 fiber fragments per cluster, about 40 fiber fragments per cluster, about 50 fiber fragments per cluster, about 60 fiber fragments per cluster, about 70 fiber fragments per cluster, about 80 fiber fragments per cluster, about 90 fiber fragments per cluster, about 100 fiber fragments per cluster, about 110 fiber fragments per cluster, about 200 fiber fragments per cluster, about 300 fiber fragments per cluster, about 400 fiber fragments per cluster, about 500 fiber fragments per cluster, about 600 fiber fragments per cluster, about 700 fiber fragments per cluster, about 800 fiber fragments per cluster, about 900 fiber fragments per cluster, about 1000 fiber fragments per cluster, or ranges between any two of these values, including endpoints.

EXAMPLES

Figure 5:
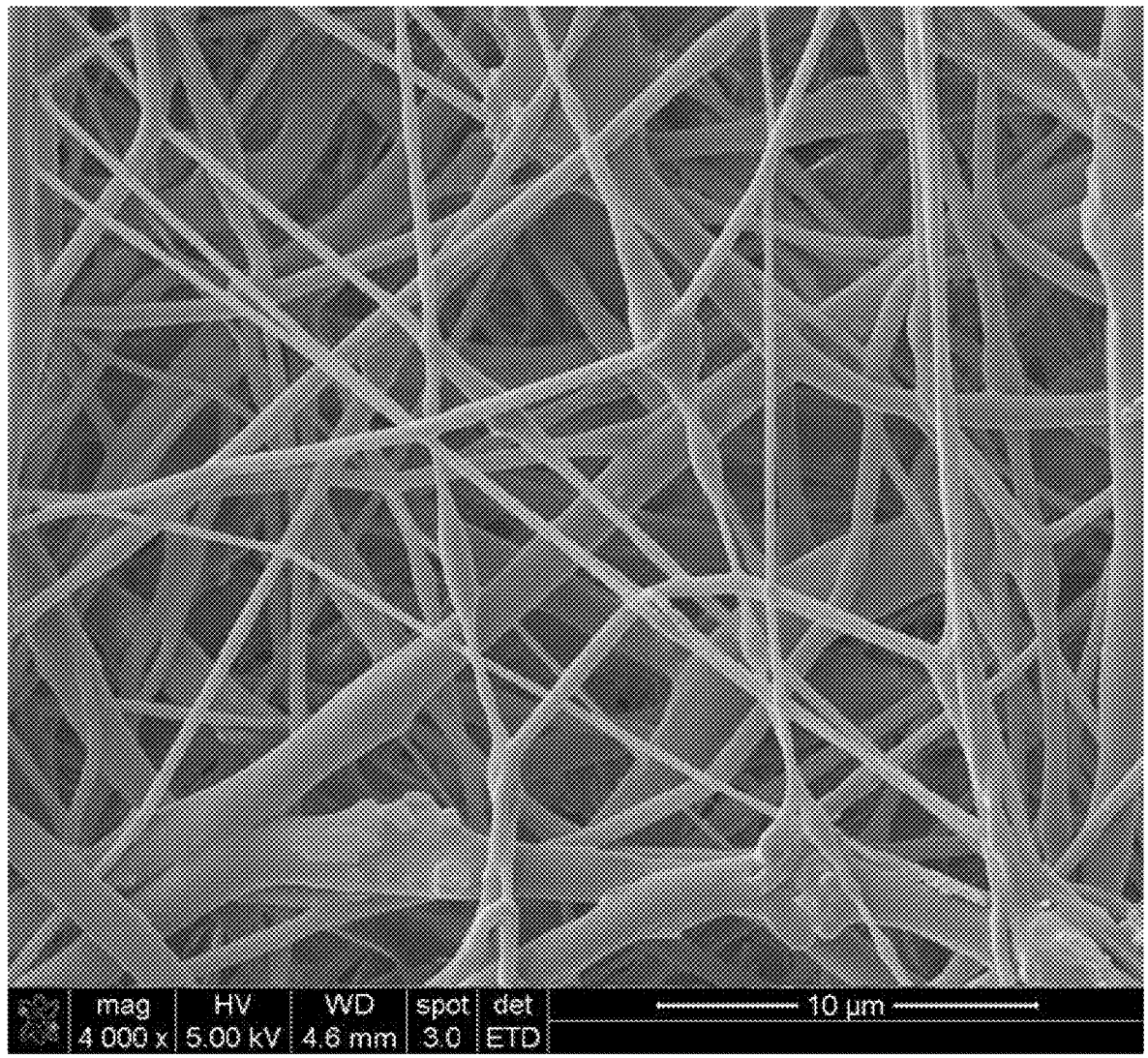
FIG. 5 is a scanning electron microscope (SEM) image of a fiber comprising a polymer and 100 wt % bismuth based on the weight of the polymer, in accordance with an embodiment of the present disclosure.

To create the fiber comprising a polymer and 100 wt % bismuth based on the weight of the polymer shown in FIG. 5, the solution weight % and total weight for the solution without the bismuth were chosen. The mass of the solvent and polymer were then calculated, and the mass of the bismuth was calculated by taking 100% of the polymer mass. The polymer and solvent were mixed in a flask until homogeneous, and the contrast agent was then added and mixed until colloidal or very well dispersed. Scanning electron microscope (SEM) images were then obtained.

Figure 6:
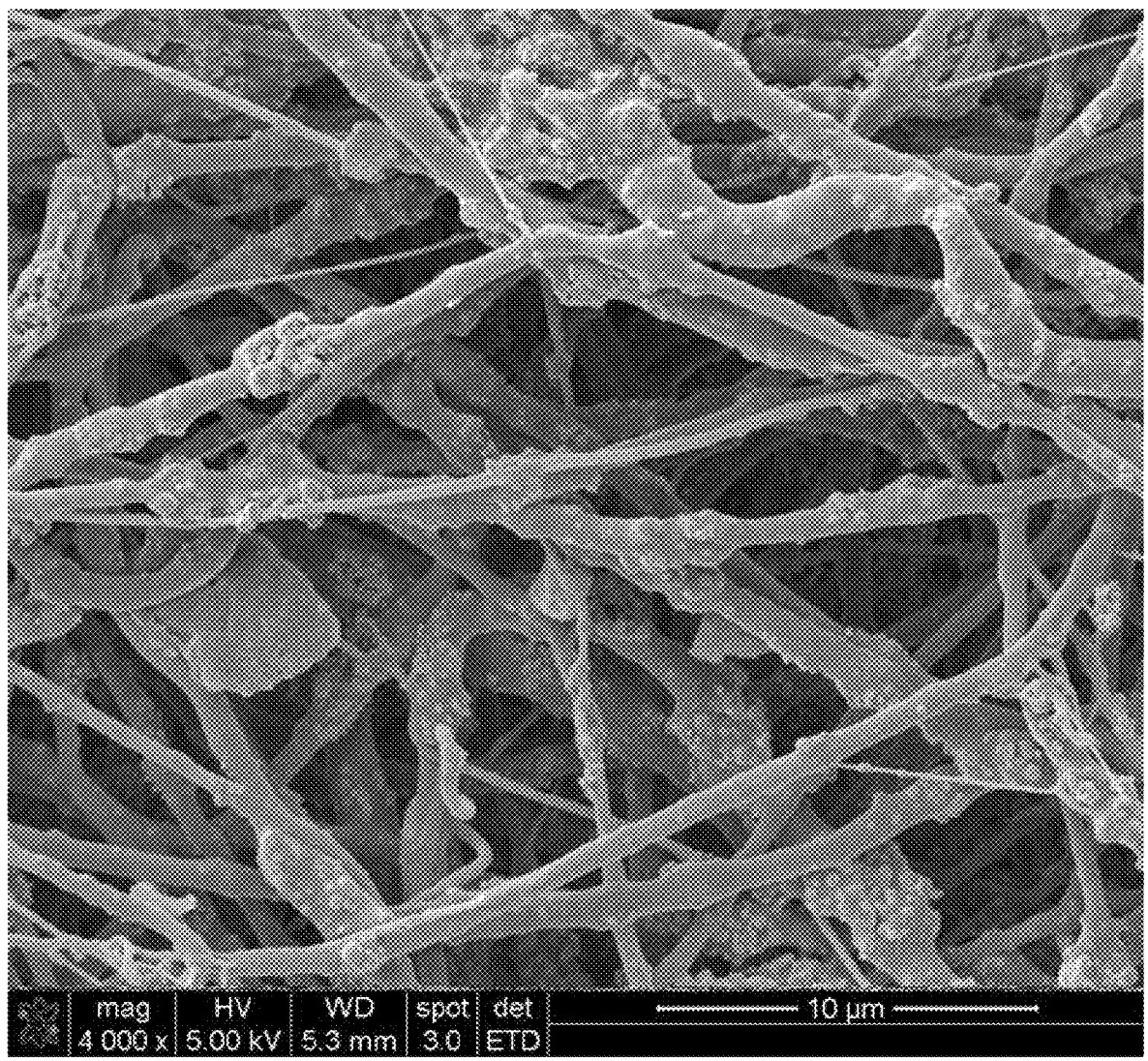
FIG. 6 is a scanning electron microscope (SEM) image of a fiber comprising a polymer and 400 wt % bismuth based on the weight of the polymer, in accordance with an embodiment of the present disclosure.

To create the fiber comprising a polymer and 400 wt % bismuth based on the weight of the polymer shown in FIG. 6, the solution weight % and total weight for the solution without the bismuth were chosen. The mass of the solvent and polymer were then calculated, and the mass of the bismuth was calculated by taking 400% of the polymer mass. The polymer and solvent were mixed in a flask until homogeneous, and the contrast agent was then added and mixed until colloidal or very well dispersed. Scanning electron microscope (SEM) images were then obtained.

Figure 7:
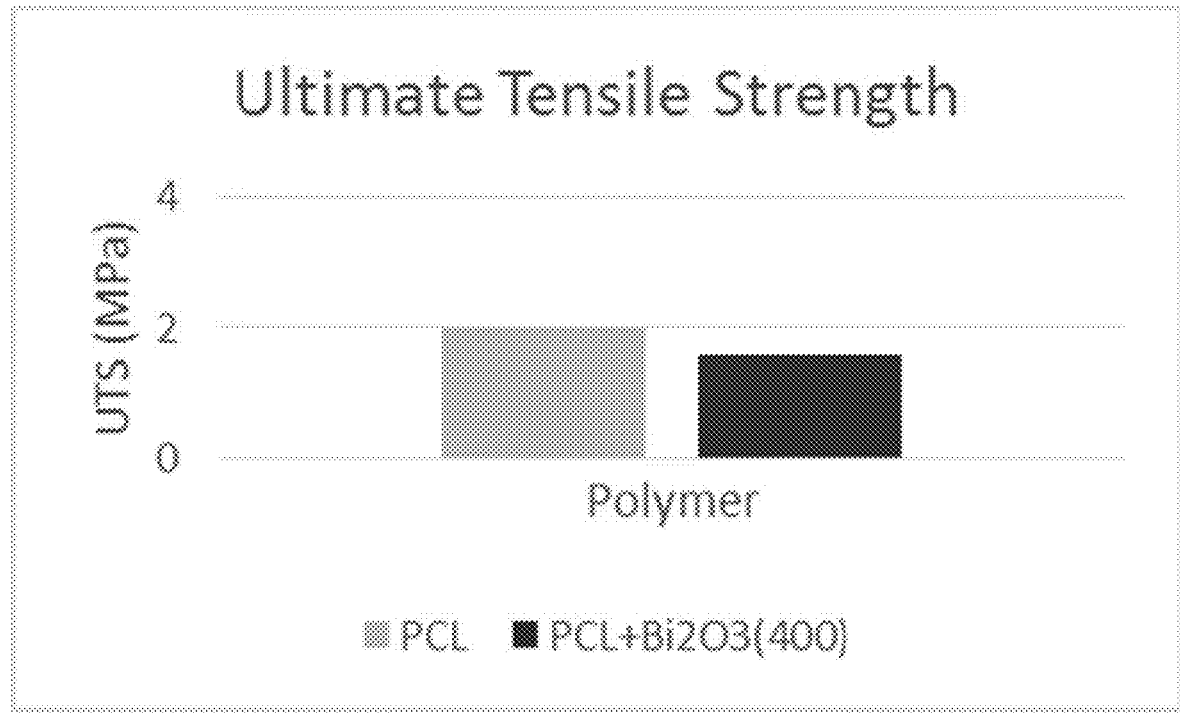
FIG. 7 graphically illustrates a comparison of the ultimate tensile strength (UTS, in MPa) of a fiber comprising polycaprolactone (PCL), and a fiber comprising PCL and 400 wt % bismuth ($Bi_2O_3$) based on the weight of the PCL, in accordance with an embodiment of the present disclosure.
Figure 8:
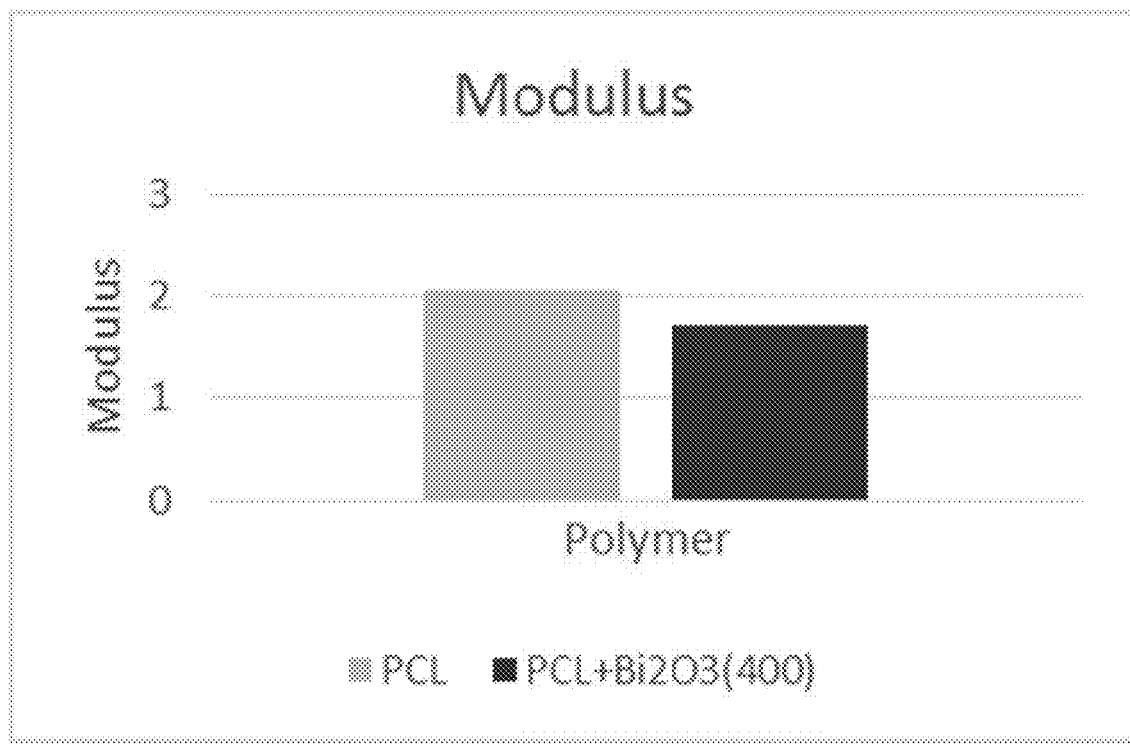
FIG. 8 graphically illustrates a comparison of the modulus of a fiber comprising PCL, and a fiber comprising PCL and 400 wt % $Bi_2O_3$ based on the weight of the PCL, in accordance with an embodiment of the present disclosure.
Figure 9:
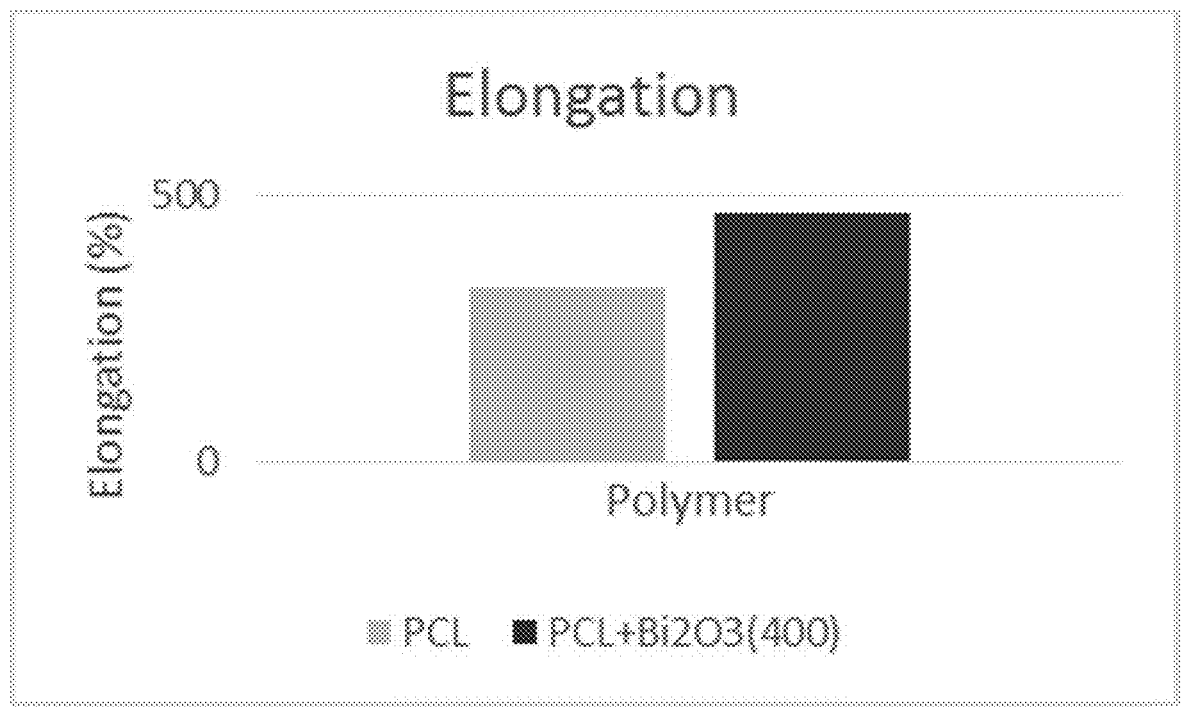
FIG. 9 graphically illustrates a comparison of the elongation (%) of a fiber comprising PCL, and a fiber comprising PCL and 400 wt % bismuth $Bi_2O_3$ based on the weight of the PCL, in accordance with an embodiment of the present disclosure.

The mechanical properties of fibers created as described above were also analyzed. FIGS. 7, 8, and 9 graphically illustrate comparisons of the ultimate tensile strength (UTS, in MPa), modulus, and elongation (%), respectively, of a fiber comprising polycaprolactone (PCL), and a fiber comprising PCL and 400 wt % bismuth ($Bi_2O_3$) based on the weight of the PCL. Generally, when adding hard particles to a soft matrix, one would expect the UTS and modulus of the resulting fiber to increase, and the % elongation to decrease. Surprisingly, the fibers in accordance with the present disclosure and their mechanical properties described in FIGS. 7, 8, and 9 displayed the opposite results. Compared to the fiber comprising PCL, the fiber comprising PCL and 400 wt % $Bi_2O_3$ displayed decreased UTS and modulus, and increased % elongation. These results were unexpected, and such mechanical properties may be useful over any previously made compositions, particularly for applications related to the repair, replacement, or treatment of any organ or tissue within the body, or for the proliferation or differentiation of cells outside the body.

Figure 10:
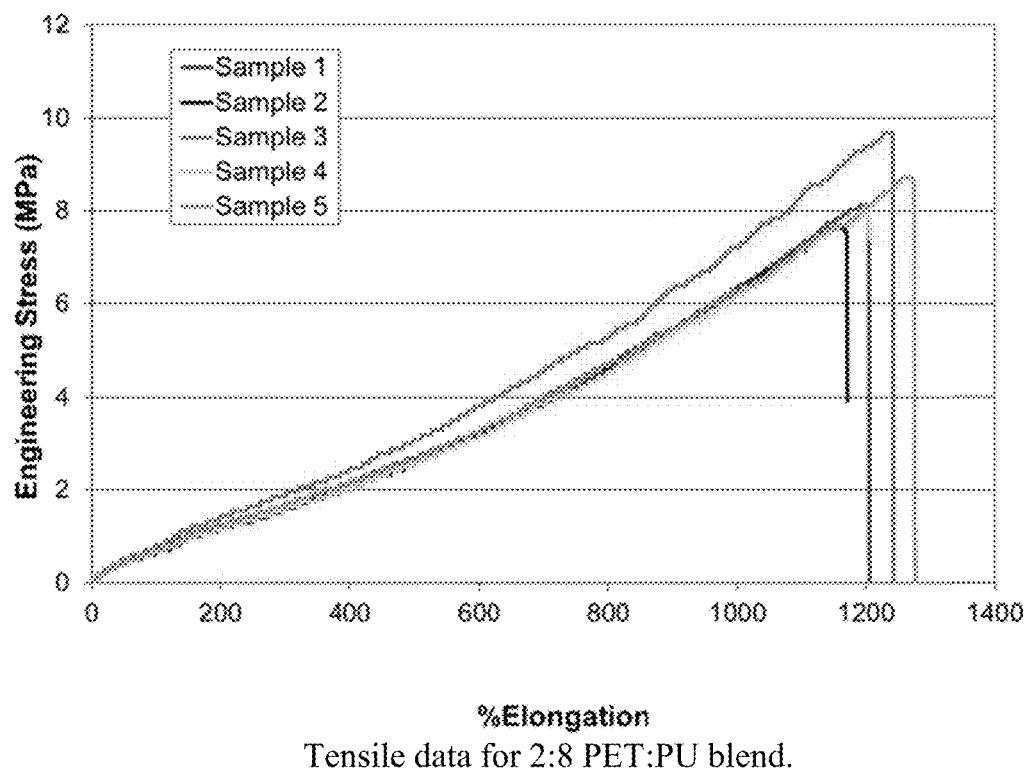
FIG. 10 graphically illustrates the engineering stress vs. elongation (%) of a five sample test set of an electrospun fiber comprising an unfilled 2:8 blend of polyethylene terephthalate and polyurethane.
Figure 11:
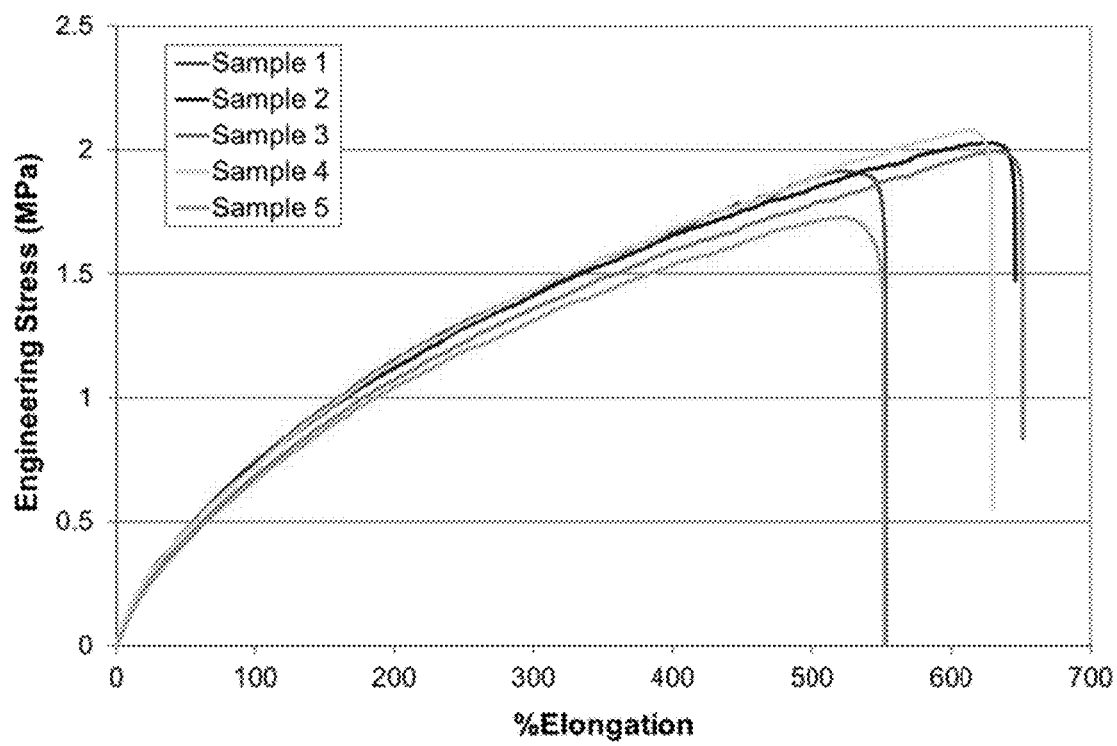
FIG. 11 graphically illustrates the engineering stress vs. elongation (%) of a five sample test set of an electrospun fiber comprising a 2:8 blend of polyethylene terephthalate and polyurethane filled with 1,000 wt % of tantalum, in accordance with an embodiment of the present disclosure.

FIG. 10 illustrates stress-strain data measured as elongation (%) versus engineering stress (MPa) of five fiber samples (Samples 1-5), each sample comprised of a 2:8 ratio of an polyethylene terephthalate to polyurethane blend without an added filler. In turn, FIG. 11 illustrates stress-strain data measured as elongation (%) versus engineering stress (MPa) of five fiber samples (Samples 1-5), each sample comprised of a 2:8 ratio of polyethylene terephthalate to polyurethane blend comprising 1,000 wt % tantalum. The filled samples illustrate that fibers comprising a filler (including a contrast agent) present at about 1,000 wt % can maintain sufficient mechanical integrity for use in the applications disclosed herein. Further, when the filler includes a contrast agent, it is apparent that the ability to have a fiber with a high wt % of contrast agent provides a much-needed benefit for non-invasively imaging the fiber. Further, it is unexpected that such a high amount of a filler (such as a contrast agent) can be incorporated into a fiber while maintaining this mechanical integrity.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

The invention claimed is:

1. A fiber comprising:
   an electrospun polymer; and
   a contrast agent present in an amount of at least about 1,000 wt % based on the weight of the electrospun polymer.

2. The fiber of claim 1, wherein the polymer is selected from the group consisting of polyethylene terephthalate, polyester, polymethylmethacrylate, polyacrylonitrile, silicone, polyurethane, polycarbonate, polyether ketone ketone, polyether ether ketone, polyether imide, polyamide, polystyrene, polyether sulfone, polysulfone, polycaprolactone, polylactic acid, polylactide-co-caprolactone, polylactide-co-glycolide, polyglycolic acid, polyglycerol sebacic, polydiol citrate, polyhydroxy butyrate, polyether amide, polydioxanone, derivatives thereof, and combinations thereof.

3. The fiber of claim 1, wherein the contrast agent is dispersed within the electrospun polymer.

4. The fiber of claim 1, wherein the contrast agent comprises a powder, the powder comprising particles having a diameter from about 10 nm to about 10 µm.

5. The fiber of claim 1, wherein the contrast agent is selected from the group consisting of barium, tantalum, tungsten, platinum, gold, bismuth, iodine, gadolinium, diatrizoate, metrizoate, ioxaglate, iopamidol, iohexol, ioxilan, iopromide, iodixanol, derivatives thereof, oxides thereof, salts thereof, and combinations thereof.

6. The fiber of claim 1, wherein the contrast agent is present in the fiber in an amount of about 1,500 wt % based on the weight of the electrospun polymer.

7. The fiber of claim 1, wherein the contrast agent comprises tantalum.

8. The fiber of claim 1, further comprising one or more of an electrically conductive material selected from the group consisting of gold, silver, iron, polyaniline, carbon black, polyacrylonitrile, graphene, and combinations thereof; a fluorescent material, a luminescent material, an antibiotic, a growth factor, a vitamin, a cytokine, a steroid, an anti-inflammatory drug, a small molecule, a sugar, a salt, a peptide, a protein, a cell factor, DNA, RNA, or a combination thereof.

9. The fiber of claim 1, having a length of about 5 µm to about 5m and a diameter of about 50 nm to about 50 µm.

10. The fiber of claim 1 formed into a shape selected from the group consisting of a fragment, a cluster, a strand, a thread, a sheet, a rope, a braid, a coil, a tube, a cylinder, a textile, and a mold of an organ.

11. The fiber of claim 1 formed into a fragment having an average length of about 1 µm to about 1000 µm, and an average diameter of about 0.1 µm to about 10 µm.

12. The fiber of claim 1 formed into a cluster having, independently, an average length of about 1 µm to about 10,000 µm, an average width of about 1 µm to about 10,000 µm, and an average height of about 1 µm to about 10,000 µm.

13. A method of making an electrospun fiber, the method comprising:
configuring a receiving surface to receive a polymer fiber;
applying a charge to one or more of the receiving surface, a polymer injection system, and a polymer solution ejected from the polymer injection system; and
depositing the polymer solution ejected from the polymer injection system onto the receiving surface;
wherein the polymer solution comprises a polymer and a contrast agent; and
wherein the contrast agent is present in an amount of at least about 1,000 wt % based on the weight of the polymer.

14. The method of claim 13, wherein the polymer is selected from the group consisting of polyethylene terephthalate, polyester, polymethylmethacrylate, polyacrylonitrile, silicone, polyurethane, polycarbonate, polyether ketone ketone, polyether ether ketone, polyether imide, polyamide, polystyrene, polyether sulfone, polysulfone, polycaprolactone, polylactic acid, polylactide-co-caprolactone, polylactide-co-glycolide, polyglycolic acid, polyglycerol sebacic, polydiol citrate, polyhydroxy butyrate, polyether amide, polydioxanone, derivatives thereof, and combinations thereof.

15. The method of claim 13, wherein the polymer is present in an amount of about 1 wt % to about 30 wt % based on the weight of the polymer solution.

16. The method of claim 13, wherein the contrast agent is present in an amount of about 1,500 wt % based on the weight of the polymer.

17. The method of claim 13, wherein the contrast agent comprises a powder, the powder comprising particles having a diameter from about 10 nm to about 10 µm.

18. The method of claim 13, wherein the contrast agent is selected from the group consisting of barium, tantalum, tungsten, platinum, gold, bismuth, iodine, gadolinium, diatrizoate, metrizoate, ioxaglate, iopamidol, iohexol, ioxilan, iopromide, iodixanol, derivatives thereof, oxides thereof, salts thereof, and combinations thereof.

19. The method of claim 13, wherein the polymer solution further comprises a solvent selected from the group consisting of acetone, dimethylformamide, dimethylsulfoxide, N-methylpyrrolidone, acetonitrile, hexanes, ether, dioxane, ethyl acetate, pyridine, toluene, xylene, tetrahydrofuran, trifluoroacetic acid, hexafluoroisopropanol, acetic acid, dimethylacetamide, chloroform, dichloromethane, water, alcohols, ionic compounds, derivatives thereof, and combinations thereof.

20. The method of claim 13, wherein the polymer solution further comprises one or more of an electrically conductive material, a fluorescent material, a luminescent material, an antibiotic, a growth factor, a vitamin, a cytokine, a steroid, an anti-inflammatory drug, a small molecule, a sugar, a salt, a peptide, a protein, a cell factor, DNA, RNA, or a combination thereof.

21. A fiber comprising:
an electrospun polymer; and
a contrast agent present in an amount of at least about 1,000 wt % based on the
weight of the electrospun polymer;
wherein the fiber is formed into a shape of a coil.

22. The fiber of claim 21, wherein the contrast agent comprises tantalum powder dispersed within the electrospun polymer.

23. The fiber of claim 22, wherein the electrospun polymer comprises a blend of polyethylene terephthalate to polyurethane blend in a 2:8 ratio.

* * * * *